US011291517B2

(12) United States Patent
Howell et al.

(10) Patent No.: US 11,291,517 B2
(45) Date of Patent: Apr. 5, 2022

(54) POCKET AND DRAPE SYSTEM FOR PROVIDING STERILE FIELDS

(71) Applicant: O&M Halyard, Inc., Mechanicsville, VA (US)

(72) Inventors: Margaret A. Howell, Atlanta, GA (US); Ann Dine, Sherrills Ford, NC (US)

(73) Assignee: O&M Halyard, Inc., Mechanisville, VA (US)

( * ) Notice: Subject to any disclaimer, the term of this patent is extended or adjusted under 35 U.S.C. 154(b) by 0 days.

(21) Appl. No.: 16/892,346

(22) Filed: Jun. 4, 2020

(65) Prior Publication Data

US 2020/0383743 A1     Dec. 10, 2020

Related U.S. Application Data

(60) Provisional application No. 62/857,854, filed on Jun. 6, 2019.

(51) Int. Cl.
*A61B 46/23*     (2016.01)
*A61B 46/00*     (2016.01)
*A61B 46/20*     (2016.01)

(52) U.S. Cl.
CPC .............. *A61B 46/23* (2016.02); *A61B 46/40* (2016.02); *A61B 2046/201* (2016.02)

(58) Field of Classification Search
CPC ......... A61B 46/00; A61B 46/10; A61B 46/20; A61B 46/23; A61B 46/30; A61B 46/40;
(Continued)

(56) References Cited

U.S. PATENT DOCUMENTS 3,741,206 A * 6/1973 Binard ................... A61B 46/00
128/853
4,476,860 A 10/1984 Collins et al.
(Continued)

FOREIGN PATENT DOCUMENTS

CN     202960791 U     6/2013
WO     WO 2018/194841 A1     10/2018

OTHER PUBLICATIONS

International Search Report and Written Opinion for PCT/US2020/036022, dated Sep. 1, 2020, 16 pages.

*Primary Examiner* — Alireza Nia
*Assistant Examiner* — Daniel A Miller
(74) *Attorney, Agent, or Firm* — Dority & Manning, P.A.

(57) ABSTRACT

A pocket and drape system which provides multiple (e.g., at least two) sterile fields and the methodology for employing said system is provided. The system includes first and second base drape materials each having upper and lower edges edge both extending in a longitudinal direction and first and second side edges both extending in a transverse direction. The first base drape material and the second base drape material also each include a longitudinal fold line. A first zone of pockets is present on a surface of the first base drape material and a second zone of pockets is present on a surface of the second base drape material. The manner in which the base drape materials are folded and joined to each other during assembly (e.g., before sterilization) maintains the sterility of the first and second zone of pockets until each zone is ready for use during a medical procedure.

21 Claims, 6 Drawing Sheets

(58) Field of Classification Search
CPC ........ A61B 2046/201; A61B 2050/318; A61B 2050/3015; A61B 2050/3008; A61B 2050/155; A61B 50/10; A61B 50/13; A61B 50/30; A61B 50/33; A61B 19/00; A61B 19/02; A61B 19/08; A61B 19/10
USPC ....... 128/849, 850, 851, 852, 853, 854, 855, 128/856; 220/528; 604/357; 206/570
See application file for complete search history.

(56) References Cited

U.S. PATENT DOCUMENTS

| | | | |
|---|---|---|---|
| 4,937,299 A | 6/1990 | Ewen et al. | |
| 5,170,804 A | 12/1992 | Glassman | |
| 5,218,071 A | 6/1993 | Tsutsui et al. | |
| 5,272,236 A | 12/1993 | Lai et al. | |
| 5,278,272 A | 1/1994 | Lai et al. | |
| 5,322,728 A | 6/1994 | Davey et al. | |
| 5,472,775 A | 12/1995 | Obijeski et al. | |
| 5,539,056 A | 7/1996 | Yang et al. | |
| 5,571,619 A | 11/1996 | McAlpin et al. | |
| 5,596,052 A | 1/1997 | Resconi et al. | |
| 6,090,325 A | 7/2000 | Wheat et al. | |
| 6,436,085 B1 | 8/2002 | Lauer | |
| 6,500,563 B1 | 12/2002 | Datta et al. | |
| 6,644,317 B1 | 11/2003 | Lawton | |
| 7,040,484 B1 * | 5/2006 | Homra | A61B 50/13 206/363 |
| 8,371,448 B1 * | 2/2013 | Reaux | A61B 46/00 206/570 |
| 10,537,707 B2 | 1/2020 | Brooks et al. | |
| 2013/0075457 A1 | 3/2013 | Sato et al. | |
| 2013/0152946 A1 * | 6/2013 | Sosnowski | A61B 46/23 128/852 |
| 2013/0193019 A1 | 8/2013 | Gluck | |
| 2013/0240399 A1 | 9/2013 | Czajka, Jr. et al. | |
| 2017/0368302 A1 | 12/2017 | Brooks et al. | |
| 2019/0038372 A1 | 2/2019 | Dine | |
| 2019/0142541 A1 * | 5/2019 | Neis | A61B 46/20 128/853 |

\* cited by examiner

POCKET AND DRAPE SYSTEM FOR PROVIDING STERILE FIELDS

RELATED APPLICATIONS

The present application claims priority to U.S. Provisional Application Ser. No. 62/857,854, filed on Jun. 6, 2019, which is incorporated herein in its entirety by reference thereto.

FIELD OF THE INVENTION

The present invention relates to sterile compartmentalized packaging. The present invention further relates to sterile compartmentalized packaging containing supplies for use in medical procedures. The present invention further relates to any procedure with multiple steps required in a sterile field in order to minimize infections, bacterial or other.

BACKGROUND OF THE INVENTION

It is well known that medical procedures require sterile supplies and/or instruments in order to avoid infections. Every year, an estimated 650,000 people in the United States develop infections during a hospital stay and about 75,000 die, according to the Centers for Disease Control and Prevention (CDC). More specifically, more than 8,000 patients are killed by MRSA (methicillin-resistant *Staphylococcus aureus*). Still another bacteria, C. diff (*Clostridium difficile*), kills approximately 27,000 patients in the U.S. annually while causing sickness in about 290,000 patients. These are but two of the many infectious diseases waiting to strike down patients in U.S. hospitals today. But treatment is often provided outside of hospitals, so there exists a need to provide a sterile environment in any place where various medical procedures are conducted such as clinics, ambulances, on the street, at home, and even on the battlefield.

Care providers often use individually packaged medical supply kits that include all the medical supplies necessary for a medical procedure bundled in a single package. Many medical procedures are staged procedures, wherein some medical items or supplies in a sterile condition are required at one time period during the medical procedure and other additional medical items in a sterile condition are required at a future time period, such as minutes, hours, or days later. In these situations, use of individually packaged medical supplies is not desirable and, once opened, kits and/or trays containing the required medical supplies that are needed during a first time period suffer the fate of having the items required in future time periods become exposed to the environment and pose a health risk when used in the future for lack of sterility.

Typically, suppliers have placed components in a kit according to specific guidelines, stacked in order of use from top to bottom. During shipping, however, these odd sized components can shift inside the kit making the stack awkward and challenging to determine the correct order of the components. Therefore, there is also a need for products and procedures for organizing the components used in staged protocol in the correct order, sequencing them to make it easier for users to follow a step by step process, and maintaining a sterile environment near the incision site, wound, or person.

SUMMARY OF THE INVENTION

The present invention relates to a sterile compartmented packaging and procedures for using same. In particular, the present invention encompasses a system, kit, or packaging system that keeps medical supplies and/or instruments used in a multi-step sequential procedure sterile so that the necessary medical supplies and/or instruments for a given stage can be accessed in stages as needed without sacrificing the sterility of the medical supplies and/or instruments. The present invention encompasses at least one sterile field or zone (e.g., such as at least two sterile fields) in a single use pocket and drape system kit.

The present invention provides a system that includes two base drape materials having two or more zones of clear or transparent pockets intended to hold medical components in order of use according to hospital procedural protocol in a two (or multi) part procedure. The manner and order in which the first base drape material and the second base drape material are folded and joined to each other separates the system into two distinct sterile fields or zones (e.g., a first sterile field associated with a first zone of pockets containing various medical supplies and/or instruments on a surface of the first base drape material and a second sterile field associated with a second zone of pockets containing various medical supplies and/or instruments on a surface of the second base drape material).

In one particular embodiment, the present invention is directed to a pocket and drape system that includes a first base drape material having an upper edge and a lower edge both extending in a longitudinal direction and a first side edge and a second side edge both extending in a transverse direction to define a perimeter, wherein the first base drape material includes a first longitudinal fold line; a second base drape material having an upper edge and a lower edge both extending in a longitudinal direction and a first side edge and a second side edge both extending in a transverse direction to define a perimeter, where the second base drape material includes a second longitudinal fold line; a first zone of pockets located on a surface of the first base drape material; and a second zone of pockets located on a surface of the second base drape material. Further, a portion of the first base drape material adjacent the first longitudinal fold line is temporarily joined to a portion of the second based drape material adjacent the upper edge of the second base drape material, and a first transverse fold line and a second transverse fold line extend from the upper edge of the first base drape material to the lower edge of the second base drape material.

In another embodiment, the first zone of pockets and the second zone of pockets can be formed from a clear material.

In still another embodiment, a plurality of vertical seals can be present in the first zone of pockets and the second zone of pockets to define individual pockets in each of the first zone of pockets and the second zone of pockets.

In yet another embodiment, the first zone of pockets, the second zone of pockets, or both can include a free end and a sealed end.

In an additional embodiment, the first longitudinal fold line can divide the first base drape material into an upper section and a lower section each having an inner surface and an outer surface, where the first zone of pockets can be present on the inner surface of the upper section, the inner surface of the lower section, or both. Further, the inner surface of the upper section, the inner surface of the lower section, or both can include an attachment means to adhere the inner surface of the upper section to the inner surface of the lower section.

In one more embodiment, the second longitudinal fold line can divide the second base drape material into an upper section and a lower section each having an inner surface and an outer surface, wherein the second zone of pockets can be present on the inner surface of the upper section, the inner surface of the lower section, or both.

In yet another embodiment, the first base drape material and the second drape material can be separable from each other via a tearable feature extending in the longitudinal direction adjacent the first longitudinal fold line and the upper edge of the second base drape material.

In one more embodiment, a boundary can exist between the perimeter of the first base drape material and the first zone of pockets, the second base drape material and the second zone of pockets, or both. For instance, the boundary can span a distance ranging from about 40 millimeters to about 150 millimeters.

In an additional embodiment, the first base drape material, the second base drape material, or both can be formed from a sterilization material. Further, the sterilization material can be a spunbond-meltblown-spunbond (SMS) material.

In another embodiment, the first zone of pockets and the second zone of pockets can contain instruments, medical supplies, or a combination thereof for use in a multi-step sequential procedure. For example, the multi-step sequential procedure can be selected from procedures for abdominal aortic aneurysm repair; limb amputation; appendix surgery; AV shunt for dialysis; bile duct, liver, or pancreatic surgery; breast surgery; cardiac surgery; coronary bypass with chest and donor incisions; coronary bypass graft; carotid endarterectomy; gallbladder surgery; colon surgery; craniotomy; cesarean section; spinal fusion; open reduction of fracture; gastric surgery; herniorrhaphy; hip prosthesis; heart transplant; abdominal hysterectomy; knee prosthesis; kidney transplant; lam inectomy; liver transplant; neck surgery; kidney surgery; ovarian surgery; pacemaker surgery; prostate surgery; peripheral vascular bypass surgery; rectal surgery; small bowel surgery; spleen surgery; thoracic surgery; thyroid and/or parthyroid surgery; vaginal hysterectomy; ventricular shunt; and exploratory laparotomy.

In another particular embodiment, the present invention is directed to a method for maintaining a sterile field while performing a multi-step sequential procedure. The method includes the steps of providing a pocket and drape system including a first base drape material having an upper edge and a lower edge both extending in a longitudinal direction and a first side edge and a second side edge both extending in a transverse direction to define a perimeter, where the first base drape material includes a first longitudinal fold line, where a first zone of pockets is located on a surface of the first base drape material; providing a second base drape material having an upper edge and a lower edge both extending in a longitudinal direction and a first side edge and a second side edge both extending in a transverse direction to define a perimeter, where the second base drape material includes a second longitudinal fold line, where a second zone of pockets is located on a surface of the second base drape material; folding the first base drape material at the first longitudinal fold line to cover any instruments, medical supplies, or a combination thereof so that the instruments, medical supplies, or a combination thereof contained in the first zone of pockets are available for use first during the multi-step sequential procedure after unfolding the first base drape material at the first longitudinal fold line; and folding the second base drape material at the second longitudinal fold line to cover any instruments, medical supplies, or a combination thereof so that the instruments, medical supplies, or a combination thereof contained in the second zone of pockets are available for use after unfolding the second base drape material at the second longitudinal fold line, where a portion of the first base drape material adjacent the first longitudinal fold line is temporarily joined to a portion of the second based drape material adjacent the upper edge of the second base drape material.

In another embodiment, the first longitudinal fold line can divide the first base drape material into an upper section and a lower section each having an inner surface and an outer surface, where the first zone of pockets can be present on the inner surface of the upper section, the inner surface of the lower section, or both, Further, the inner surface of the upper section, the inner surface of the lower section, or both can include an attachment means to adhere the inner surface of the upper section to the inner surface of the lower section.

In yet another embodiment, the second longitudinal fold line can divide the second base drape material into an upper section and a lower section each having an inner surface and an outer surface, where the second zone of pockets can be present on the inner surface of the upper section, the inner surface of the lower section, or both.

In still another embodiment, the first base drape material and the second drape material can be separable from each other via a tearable feature extending in the longitudinal direction adjacent the first longitudinal fold line and adjacent the upper edge of the second base drape material.

In another embodiment, each of the first zone of pockets, the second zone of pockets, or both can be formed from a clear material, where a plurality of vertical seals can be present in the first zone of pockets, the second zone of pockets, or both to define individual pockets in the first zone of pockets, the second zone of pockets, or both.

In still another embodiment, the first zone of pockets, the second zone of pockets, or both can include a free end and a sealed end.

In yet another embodiment, a boundary can exist between the perimeter of the first base drape material and the first zone of pockets, the second base drape material and the second zone of pockets, or both, where the boundary can span a distance ranging from about 40 millimeters to about 150 millimeters. In one more embodiment, the first base drape material, the second base drape material, or both can be formed from a sterilization material, where the sterilization material can be a spunbond-meltblown-spunbond (SMS) material.

In an additional embodiment, the multi-step sequential procedure can be selected from procedures for abdominal aortic aneurysm repair; limb amputation; appendix surgery; AV shunt for dialysis; bile duct, liver, or pancreatic surgery; breast surgery; cardiac surgery; coronary bypass with chest and donor incisions; coronary bypass graft; carotid endarterectomy; gallbladder surgery; colon surgery; craniotomy; cesarean section; spinal fusion; open reduction of fracture; gastric surgery; herniorrhaphy; hip prosthesis; heart transplant; abdominal hysterectomy; knee prosthesis; kidney transplant; lam inectomy; liver transplant; neck surgery; kidney surgery; ovarian surgery; pacemaker surgery; prostate surgery; peripheral vascular bypass surgery; rectal surgery; small bowel surgery; spleen surgery; thoracic surgery; thyroid and/or parthyroid surgery; vaginal hysterectomy; ventricular shunt; and exploratory laparotomy.

The present invention ensures that users follow protocol/formulary exactly and reduces the risk of harm or spread of infection to the patient during medical care procedures.

The present invention also ensures that users follow protocol/formulary exactly and is designed to reduce the risk of harm or spread of infection during veterinary procedures.

Further, the present invention ensures that users follow protocol/formulary exactly and is designed to reduce the risk of harm or spread of infection during dental procedures.

The present invention further provides kits and procedures for use in research, lab testing, pharmaceutical testing, manufacturing, and the like.

One embodiment of the present invention encompasses IV start kits and procedures.

A further embodiment of the present invention encompasses central line dressing change kits and procedures. In addition, central line insertion and removal kits and procedures are also contemplated by the present invention.

A further embodiment of the present invention encompasses port access change kits and procedures. In addition, central line insertion and removal kits and procedures are also contemplated by the present invention.

A further embodiment of the present invention encompasses change kits and procedures for the veterinary field.

A further embodiment of the present invention encompasses change kits and procedures related to related dental care/dental procedures.

A further embodiment of the present invention encompasses change kits and procedures related to lab testing/lab procedures.

A further embodiment of the present invention encompasses change kits and procedures related to human or animal research testing.

A further embodiment of the present invention encompasses change kits and procedures related to pharmaceutical testing/manufacturing/research/delivery.

The present invention further contemplates a portable sterile field on a battlefield or other unsanitized place/area.

The present invention further contemplates kits customizable for any procedure requiring one or more sterile supplies or instruments.

Embodiments of the present invention also encompass change kits and procedures related to laceration and suture removal kits, disposable instrument kits, amenity kits, endoscopy kits, trach trays, and blood culture kits.

Embodiments of the present invention also encompass kits and procedures for abdominal aortic aneurysm repair; limb amputation; appendix surgery; AV shunt for dialysis; bile duct, liver, or pancreatic surgery; breast surgery; cardiac surgery; coronary bypass with chest and donor incisions; coronary bypass graft; carotid endarterectomy; gallbladder surgery; colon surgery; craniotomy; cesarean section; spinal fusion; open reduction of fracture; gastric surgery; herniorrhaphy; hip prosthesis; heart transplant; abdominal hysterectomy; knee prosthesis; kidney transplant; lam inectomy; liver transplant; neck surgery; kidney surgery; ovarian surgery; pacemaker surgery; prostate surgery; peripheral vascular bypass surgery; rectal surgery; small bowel surgery; spleen surgery; thoracic surgery; thyroid and/or parthyroid surgery; vaginal hysterectomy; ventricular shunt; and exploratory laparotomy.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE FIGURES

A full and enabling disclosure of the present invention, including the best mode thereof, directed to one of ordinary skill in the art, is set forth in the specification, which makes reference to the appended figures, in which.

DEFINITIONS

Figure 1:
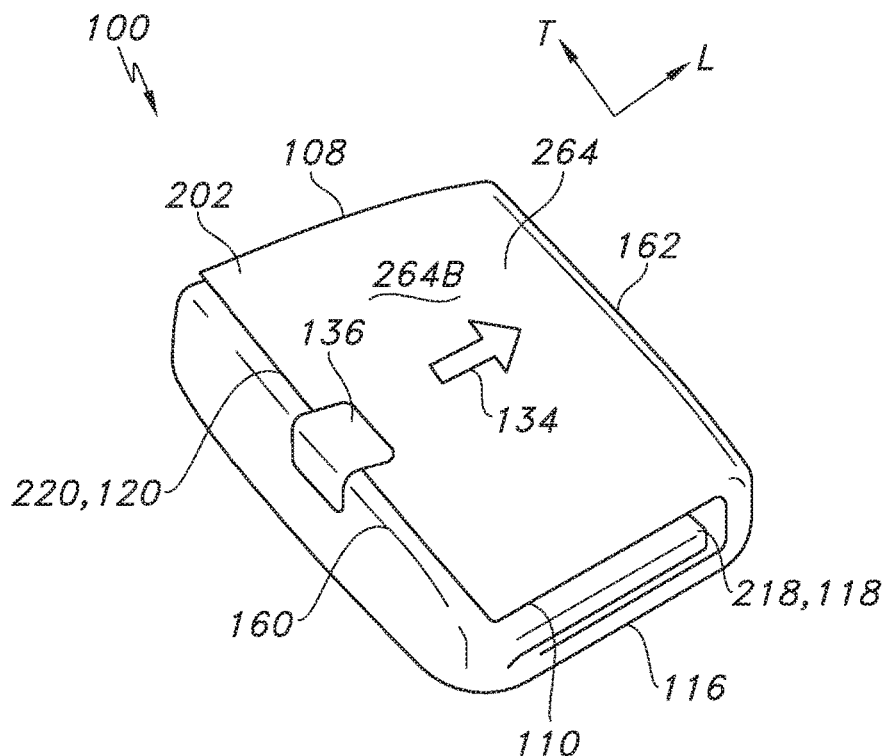
FIG. 1 illustrates a top perspective view of one embodiment of the pocket and drape system of the present invention, where the system is ready for use in a procedure after it has been folded, sealed, and sterilized.

As used herein, the term "sterilization material" refers to a flexible article composed of fabric(s) and/or flexible material(s) that is wrapped around, folded around or otherwise encloses a non-sterile article or non-sterile content prior to sterilization. Sterilization material may have multiple panels and/or sections providing specific physical properties, functional characteristics and/or structure that provide advantages for wrapping or folding, handling, strength, sterilization, storage after sterilization, and/or unwrapping or unfolding.

As used herein, the term "nonwoven web" refers to a web that has a structure of individual fibers or filaments which are interlaid, but not in an identifiable repeating manner. Nonwoven webs have been, in the past, formed by a variety of processes known to those skilled in the art such as, for example, meltblowing, spunbonding, and bonded carded web processes.

As used herein, the term "spunbond material" refers to a nonwoven material containing a web of small diameter fibers and/or filaments which are formed by extruding a molten thermoplastic material as filaments from a plurality of fine, usually circular, capillaries in a spinnerette with the diameter of the extruded filaments then being rapidly reduced, for example, by non-eductive or eductive fluid-drawing or other well-known spunbonding mechanisms.

As used herein, the term "meltblown material" refers to a nonwoven material containing fibers formed by extruding a molten thermoplastic material through a plurality of fine, usually circular, die capillaries as molten threads or filaments into a high-velocity gas (e.g. air) stream which attenuates the filaments of molten thermoplastic material to reduce their diameters, which may be to microfiber diameter. Thereafter, the meltblown fibers are carried by the high-velocity gas stream and are deposited on a collecting surface to form a web of randomly disbursed meltblown fibers.

As used herein, the term "SMS laminate material" refers to fabric laminates of spunbond and meltblown materials. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 osy to 12 osy (about 3.4 gsm to about 406 gsm), or more particularly from about 0.75 to about 3 osy (about 25.4 gsm to about 101.7 gsm).

DETAILED DESCRIPTION OF THE INVENTION

For simplicity and illustrative purposes, the principles of the present invention are described by referring to various exemplary embodiments thereof. Although the preferred embodiments of the invention are particularly disclosed herein, one of ordinary skill in the art will readily recognize that the same principles are equally applicable to, and can be implemented in other systems, and that any such variation would be within such modifications that do not part from the scope of the present invention. Before explaining the disclosed embodiments of the present invention in detail, it is to be understood that the invention is not limited in its application to the details of any particular arrangement shown, since the invention is capable of other embodiments. The terminology used herein is for the purpose of description and not of limitation. Further, although certain methods are described with reference to certain steps that are presented herein in certain order, in many instances, these steps may be performed in any order as would be appreciated by one skilled in the art, and the methods are not limited to the particular arrangement of steps disclosed herein.

The present invention is particularly useful for medical procedures that require one or more sterile fields. The present invention provides a drape with clear pockets and includes at least two sterile fields or zones intended to hold medical components in order of use according to hospital procedural protocol in a two-part or multi-part procedure. The particular manner in which the drape is folded prior to sterilization and then subsequently unfolded after sterilization separates the drape into at least two sterile fields or zones.

For instance, during a multi-part procedure that requires aseptic technique in which the pocket and drape system of the present invention is utilized, a sterile first zone of pockets located on a first base drape material and containing the appropriate medical components can be used in a first part of the procedure after unfolding the drape at multiple (e.g., two or more) transverse or vertical fold lines and then at a first longitudinal or horizontal fold line. Once the first part of the procedure is complete, the first base drape material can be removed from the system and a sterile second zone of pockets located on a second base drape material and containing the appropriate medical components can be used in a second part of the procedure after unfolding the drape at a second longitudinal or horizontal fold line.

In one particular embodiment, an exemplary kit in accordance with the present invention may include first and second base drape or wrap materials that each include one or more clear or transparent pockets in one or more zones present on a surface of the base drape material, where each of the zones can include one or more rows of pockets that can be used to hold various medical supplies (e.g., instruments, wipes, gauze, tape, medications, etc.)

Referring now to FIGS. 1-7, the various features of the pocket and drape system 100 of the present invention will be described in more detail. Turning first to FIG. 1, one embodiment of the pocket and drape system 100 of the present invention is shown, where the pocket and drape system 100 is ready for use in a multi-step procedure after it has been assembled to contain the desired medical supplies, folded, sealed, and sterilized.

As shown in FIGS. 1-7, the pocket and drape system 100 includes a first base drape material 102 and a second base drape material 202 that can be formed from a sterilization material, which can be any suitable nonwoven material. In one particular embodiment, the first base drape material 102 and the second base drape material 202 can be in the form of a spunbond-meltblown-spunbond (SMS) laminate material. In one particular embodiment, the SMS laminate material can include a first spunbond layer and a second spunbond layer with a meltblown layer disposed therebetween. In some embodiments, the spunbond layers can be formed from a semi-crystalline polyolefin. Exemplary polyolefins may include, for instance, polyethylene, polypropylene, blends and copolymers thereof. In one particular embodiment, a polyethylene is employed that is a copolymer of ethylene and an α-olefin, such as a $C_3$-$C_{20}$ α-olefin or $C_3$-$C_{12}$ α-olefin. Suitable α-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin co-monomers are 1-butene, 1-hexene and 1-octene. The ethylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %.

The density of the polyethylene may vary depending on the type of polymer employed, but generally ranges from 0.85 to 0.96 grams per cubic centimeter ("g/cm$^3$"). Polyethylene "plastomers", for instance, may have a density in the range of from 0.85 to 0.91 g/cm$^3$. Likewise, "linear low density polyethylene" ("LLDPE") may have a density in the range of from 0.91 to 0.940 g/cm$^3$; "low density polyethylene" ("LDPE") may have a density in the range of from 0.910 to 0.940 g/cm$^3$; and "high density polyethylene" ("HDPE") may have density in the range of from 0.940 to 0.960 g/cm$^3$. Densities may be measured in accordance with ASTM 1505. Particularly suitable ethylene-based polymers for use in the present invention may be available under the designation EXACT™ from ExxonMobil Chemical Company of Houston, Tex. Other suitable polyethylene plastomers are available under the designation ENGAGE™ and AFFINITY™ from Dow Chemical Company of Midland, Mich. Still other suitable ethylene polymers are available from The Dow Chemical Company under the designations DOWLEX™ (LLDPE) and ATTANE™ (ULDPE). Other suitable ethylene polymers are described in U.S. Pat. No. 4,937,299 to Ewen et al.; U.S. Pat. No. 5,218,071 to Tsutsui et al.; U.S. Pat. No. 5,272,236 to Lai, et al.; and U.S. Pat. No. 5,278,272 to Lai, et al., which are incorporated herein in their entirety by reference thereto for all purposes.

Of course, the spunbond layers of the SMS laminate material from which the first base drape material 102 and the second base drape material 202 are formed are by no means limited to ethylene polymers. For instance, propylene polymers may also be suitable for use as a semi-crystalline polyolefin. Suitable propylene polymers may include, for instance, polypropylene homopolymers, as well as copolymers or terpolymers of propylene with an α-olefin (e.g., $C_3$-$C_{20}$) comonomer, such as ethylene, 1-butene, 2-butene, the various pentene isomers, 1-hexene, 1-octene, 1-nonene, 1-decene, 1-unidecene, 1-dodecene, 4-methyl-1-pentene, 4-methyl-1-hexene, 5-methyl-1-hexene, vinylcyclohexene, styrene, etc. The comonomer content of the propylene polymer may be about 35 wt. % or less, in some embodiments from about 1 wt. % to about 20 wt. %, in some embodiments, from about 2 wt. % to about 15 wt. %, and in some embodiments from about 3 wt. % to about 10 wt. %. The density of the polypropylene (e.g., propylene/α-olefin copolymer) may be 0.95 grams per cubic centimeter (g/cm$^3$) or less, in some embodiments, from 0.85 to 0.92 g/cm$^3$, and in some embodiments, from 0.85 g/cm$^3$ to 0.91 g/cm$^3$. In one particular embodiment, the spunbond layers can each include a copolymer of polypropylene and polyethylene.

Suitable propylene polymers are commercially available under the designations VISTAMAXX™ from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Other examples of suitable propylene polymers are described in U.S. Pat. No. 6,500,563 to Datta, et al.; U.S. Pat. No. 5,539,056 to Yang, et al.; and U.S. Pat. No. 5,596,052 to Resconi, et al., which are incorporated herein in their entirety by reference thereto for all purposes.

Any of a variety of known techniques may generally be employed to form the polyolefins. For instance, olefin polymers may be formed using a free radical or a coordination catalyst (e.g., Ziegler-Natta or metallocene). Metallocene-catalyzed polyolefins are described, for instance, in U.S. Pat. No. 5,571,619 to McAlpin et at; U.S. Pat. No. 5,322,728 to Davey, et al.; U.S. Pat. No. 5,472,775 to Obiieski et al.; U.S. Pat. No. 5,272,236 to Lai et al.; and U.S. Pat. No. 6,090,325 to Wheat, et al., which are incorporated herein in their entirety by reference thereto for all purposes.

The melt flow index (MI) of the polyolefins may generally vary, but is typically in the range of about 0.1 grams per 10 minutes to about 100 grams per 10 minutes, in some embodiments from about 0.5 grams per 10 minutes to about 30 grams per 10 minutes, and in some embodiments, about 1 to about 10 grams per 10 minutes, determined at 190° C. The melt flow index is the weight of the polymer (in grams) that may be forced through an extrusion rheometer orifice (0.0825-inch diameter) when subjected to a force of 2160 grams in 10 minutes at 190° C., and may be determined in accordance with ASTM Test Method D1238-E.

The meltblown layer of the SMS laminate material can also be formed from any of the semi-crystalline polyolefins discussed above with respect to the first spunbond layer and the second spunbond layer of the laminate material. In one particular embodiment, the meltblown layer can be formed from 100% polypropylene.

Regardless of the specific polymer or polymers used to form the SMS laminate material, the SMS laminate material from which the first base drape material 102 and the second base drape material 202 are formed can have a basis weight ranging from about 5 gsm to about 50 gsm, such as from about 10 gsm to about 40 gsm, such as from about 15 gsm to about 30 gsm.

Referring now to FIGS. 1-7, the specific features of pocket and drape system 100 are described in more detail. As shown, the system 100 includes a first base drape material 102 and a second base drape material 202. When the system 100 is folded, sterilized, and ready for use, the first base drape material 102 includes a first longitudinal fold line 108 in the longitudinal or horizontal direction L, while the second base drape material 202 includes a second longitudinal fold line 110 in the longitudinal or horizontal direction L. Further, the system 100 includes a first transverse fold line 160 and a second transverse fold line 162 extending the transverse or vertical direction T. Prior to sterilization, the system 100 is folded at the first transverse fold line 160 followed by the second transverse fold line 162 and then sealed with attachment means (e.g., a safety seal) 136. Further, directional indicia 134, such as an arrow, can be placed on the system 100 to indicate the direction in which the system 100 is to be opened for use.

Figure 3:
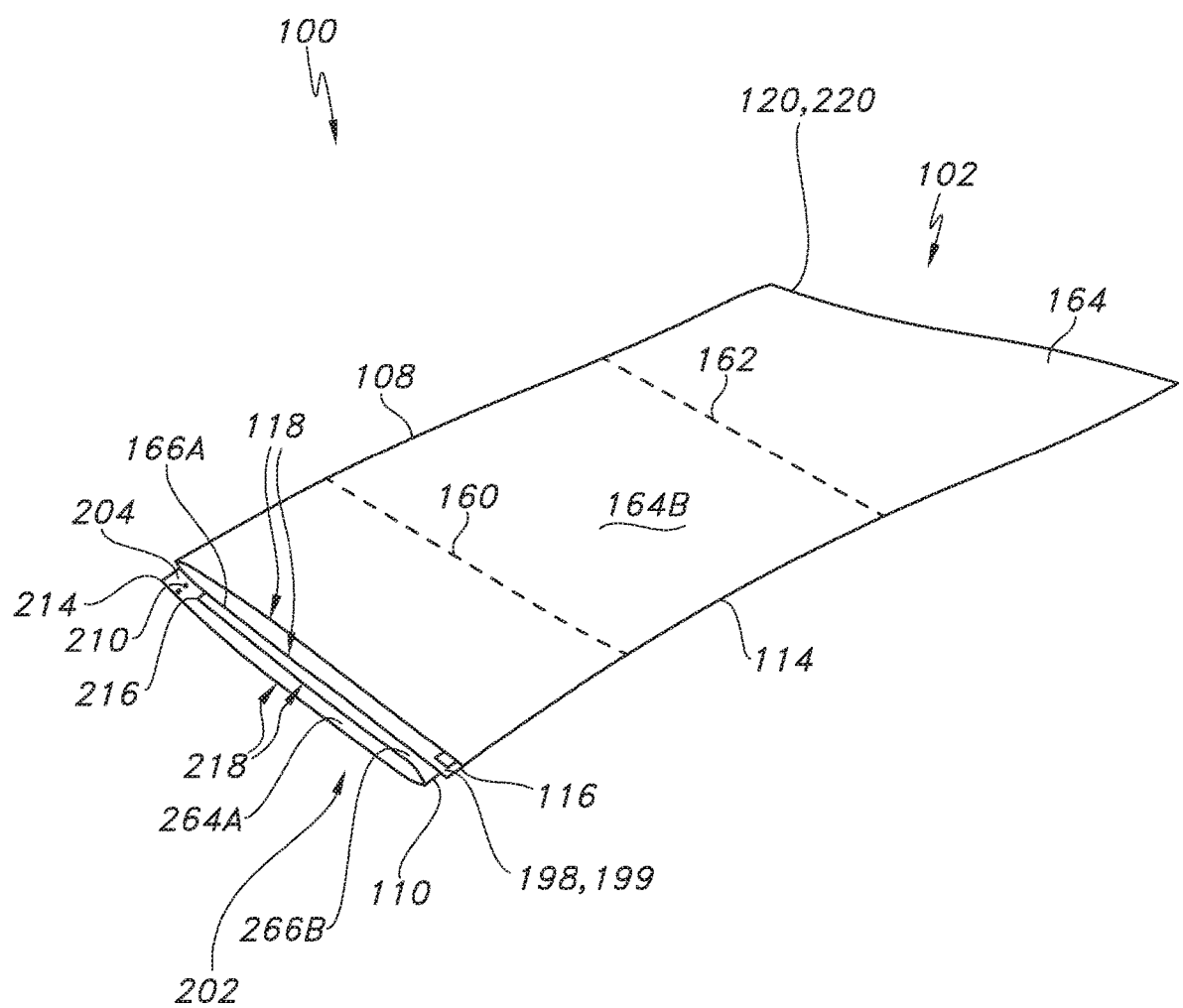
FIG. 3 illustrates a top perspective view of the pocket and drape system of FIGS. 1-2 after the pocket and drape system has been unfolded in the longitudinal or horizontal direction at first and second transverse fold lines.
Figure 4:
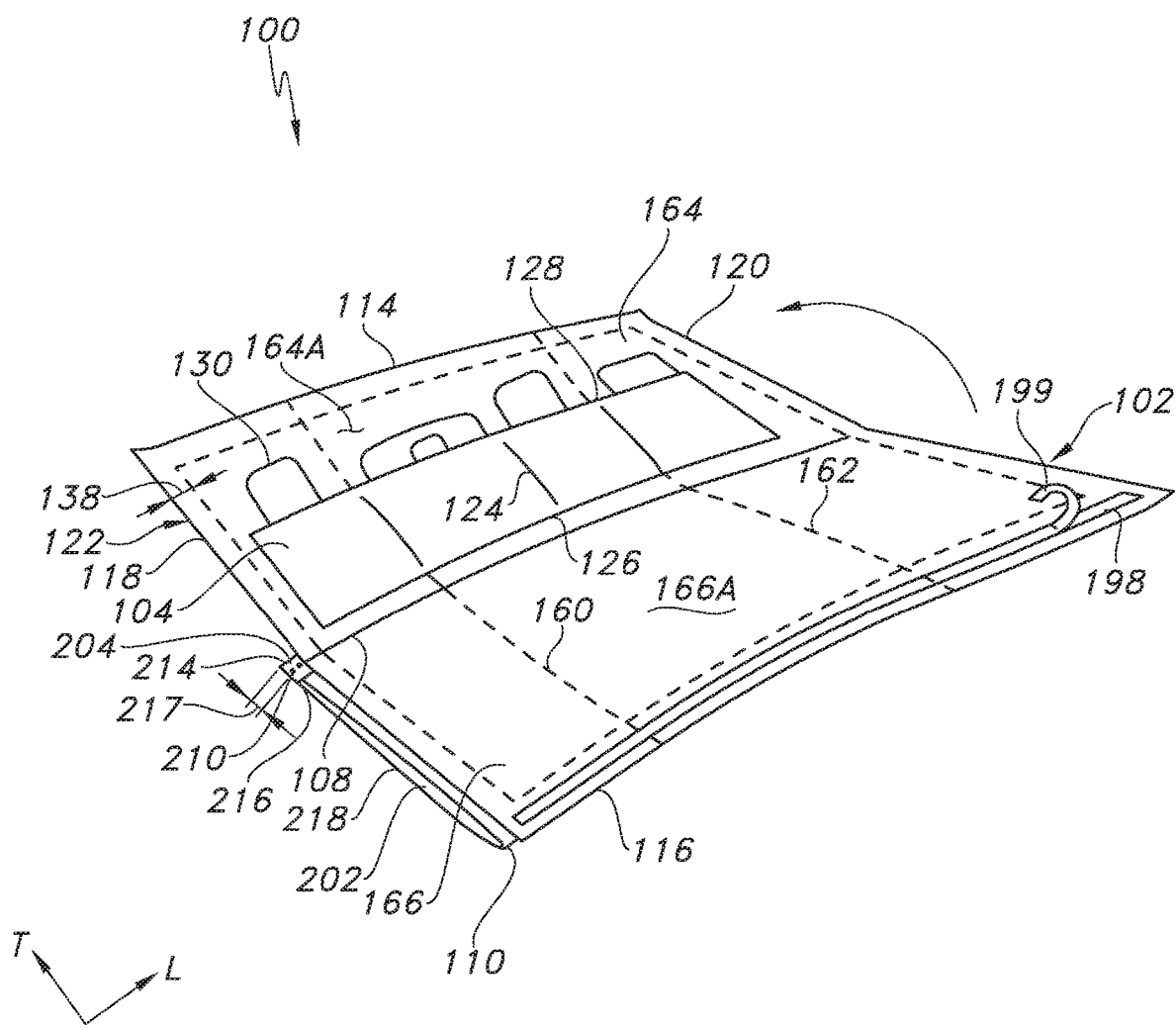
FIG. 4 illustrates a top perspective view of the pocket and drape system of FIGS. 1-3 after the first base drape material has been unfolded upwards in the transverse or vertical direction at a first longitudinal fold line to reveal a first zone of pockets present on a surface of the first base drape material that can be used in a first part of the procedure and as an optional release liner is being removed from an attachment means adjacent the lower edge of the first base drape material.

Turning now to the specific features of the first base drape material 102 and the second base drape material 202 and how they are arranged with respect to each other, the first base drape material 102 includes an upper edge 114, a lower edge 116, a first side edge 118, and a second side edge 120 to define a perimeter 122 (see FIGS. 3-4). Further, when first the base drape material 102 is folded at the first longitudinal fold line 108, the first base drape material 102 is divided into an upper section 164 and a lower section 166, where the upper section 164 includes an inner surface 164A and an outer surface 164B, while the lower section 166 includes an inner surface 166A and an outer surface 166B. Likewise, the second base drape material 202 includes an upper edge 214, a lower edge 216, a first side edge 218, and a second side edge 220 to define a perimeter 222 (see FIGS. 5-6). Further, when the second base drape material 202 is folded at the second longitudinal fold line 110, the second base drape material 202 is divided into an upper section 264 and a lower section 266, where the upper section 264 includes an inner surface 264A and an outer surface 264B, while the lower section 266 includes an inner surface 266A and an outer surface 266B. As shown in FIG. 1, when the system 100 is assembled, folded, sealed, and ready for use, the outer surface 264B of the upper section 264 of the second base drape material 202 forms the exterior of the system 100.

Figure 2:
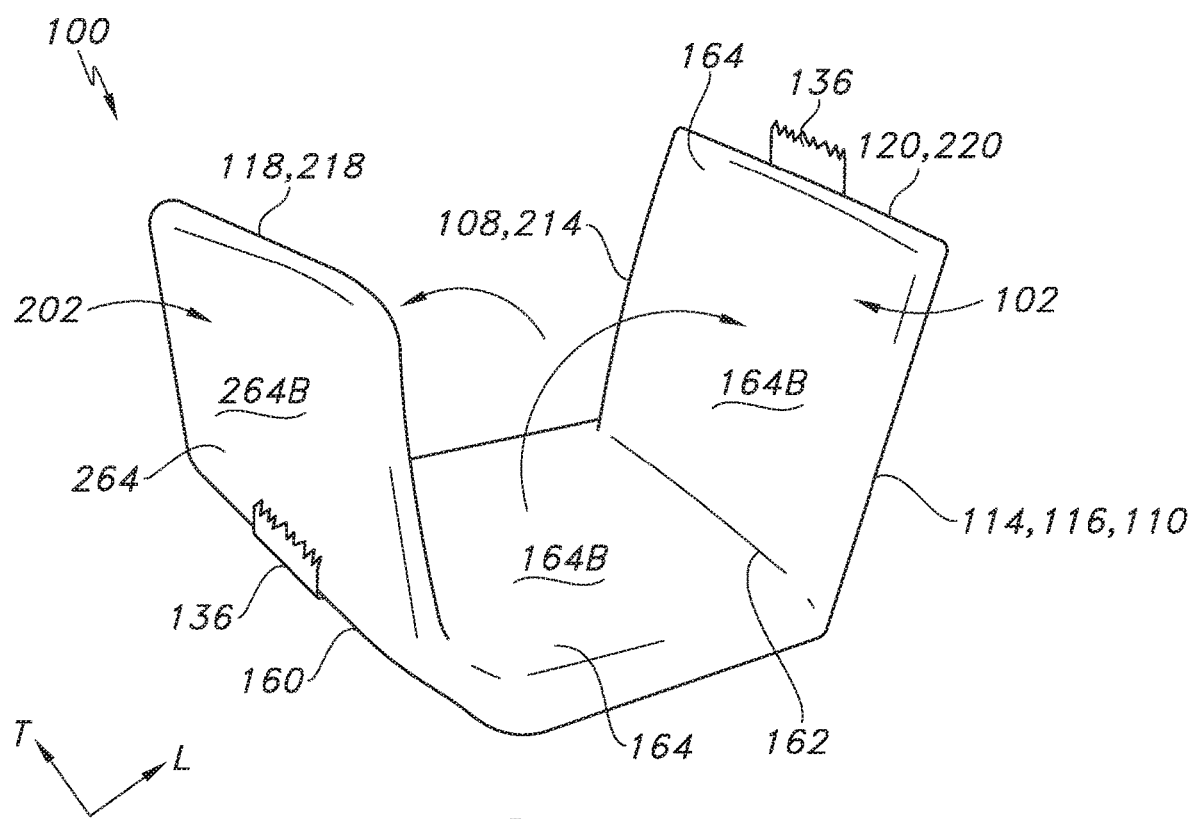
FIG. 2 illustrates a top perspective view of the pocket and drape system of FIG. 1 after removal of an attachment means and while the pocket and drape system is being unfolded in the longitudinal or horizontal direction at first and second transverse fold lines.

FIG. 2 illustrates a top perspective view of the pocket and drape system of FIG. 1 after removal of the attachment means 136 and after the pocket and drape system 100 has been unfolded in the longitudinal or horizontal direction L at the second transverse fold line 162 in the direction of the directional indicia 134, followed by unfolding the system 100 in the longitudinal or horizontal direction L at the first transverse fold line 160. As shown, the first base drape material 102 forms an interior surface of the system 100, with the outer surface 164B of the upper section 164 of the first base drape material 102 exposed, while the second base drape material 202 forms the exterior surface of the system 100, with the outer surface 264B of the upper section 264 of the second base drape material 202 exposed. Further, as shown in FIG. 3, at this point in the unfolding process, both the first base drape material 102 and the second base drape material 202 remain folded at the first longitudinal fold line 108 and the second longitudinal fold line 110, respectively, such that the first side edge 118 of the first base drape material 102 is positioned on top of the first side edge 218 of the second base drape material; the second side edge 120 of the first base drape material 102 is positioned on top of the second side edge 220 of the second base drape material 202; the first longitudinal fold line 108 is positioned on top of the upper edge 214 of the second base drape material 202; and the upper edge 114 of the first base drape material 102 is positioned on top of the lower edge 116 of the first base drape material 102, which is positioned on top of the second longitudinal fold line 110. As shown, the first longitudinal fold line 108 associated with the first base drape material 102 and the second longitudinal fold line 110 are positioned or located on opposites sides of the system 100 when the system 100 has not yet been unfolded in the transverse or vertical direction T. In other words, the first longitudinal fold line 108 faces a direction opposite the second longitudinal fold line 110.

Turning now to FIG. 4, a top perspective view of the pocket and drape system 100 of FIGS. 1-3 after the first base drape material 102 has been unfolded upwards in the transverse or vertical direction T at the first longitudinal fold line 108 to reveal a first zone of pockets 104 present on the inner surface 164A of the upper section 164 of the first base drape material 102, which can contain supplies 130 to be used in a first part of a medical procedure, is shown. Further, also shown is an optional release liner 199 as it is being removed from an attachment means 198 adjacent the lower edge 116 of the first base drape material 102, although it is to be understood that the optional release liner 199 and the attachment means 198 can alternatively be present adjacent the upper edge 114 of the first base drape material 102, the use of which is discussed in more detail with respect to FIG. 5.

In FIG. 4, the first zone of pockets 104 (which can include multiple rows, not shown) is illustrated as being disposed on the inner surface 164A of the upper section 164 of the first base drape material 102, although it is to be understood that the first zone of pockets 104 can alternatively be disposed on the inner surface 166A of the lower section 166 of the first base drape material 102, or the first zone of pockets 104 can be present on both the inner surface 164A and the inner surface 166B. In any event, the first zone of pockets 104 is positioned on the first base drape material 102 such that a boundary 138 between the perimeter 122 of the base drape material 102 as defined by upper edge 114, first side edge 118, lower edge 116, and second side edge 120 and the first zone of pockets 104 spans a distance in the longitudinal L direction and the transverse T direction of at least about 40 millimeters, such as at least about 45 millimeters, such as at least about 50 millimeters. For instance, boundary 138 between the perimeter 122 of the first base drape material 102 and the first zone of pockets 104 can span a distance ranging from about 40 millimeters to about 150 millimeters, such as from about 45 millimeters to about 125 millimeters, such as from about 50 millimeters to about 100 millimeters. Without intending to be limited by any particular theory, the present inventors have found that a boundary 138 spanning such a distance can help in maintaining the sterility of the system 100.

Figure 5:
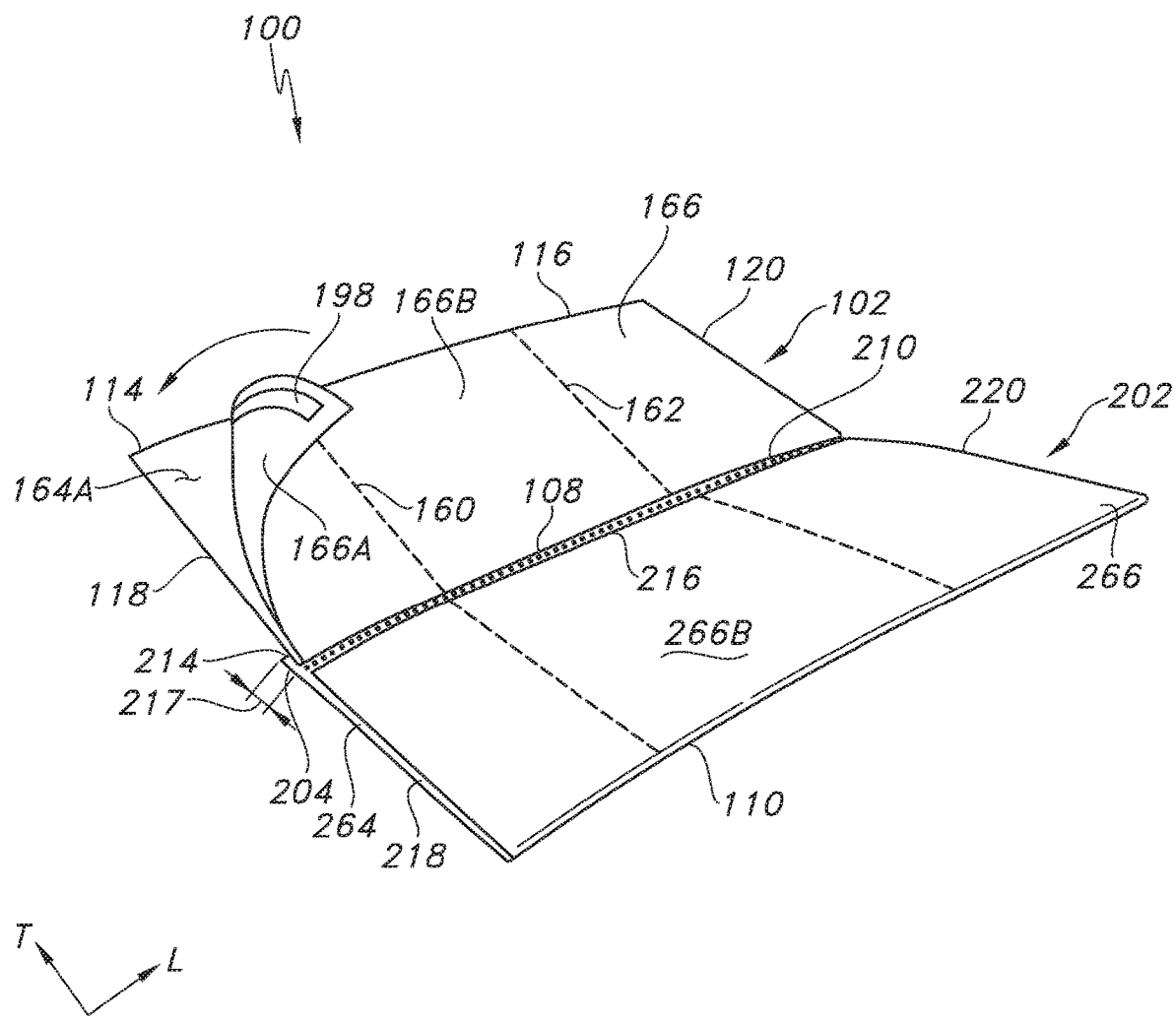
FIG. 5 illustrates a top perspective view of the pocket and drape system of FIGS. 1-4 after the optional release liner has been removed from the attachment means adjacent the lower edge of the first base drape material and the first base drape material is folded upwardly in the transverse or vertical direction from the lower edge towards the first longitudinal fold line such that a portion of the first base drape material covers the first zone of pockets present on another portion of the first base drape material and the attachment means can be used to seal the portions of the first base drape material together.

Also shown in FIG. 4 is the manner in which the first base drape material 102 and the second base drape material 202 can be joined to each other, which can also be seen in FIGS. 3 and 5. For example, the first base drape material 102 and the second base drape material 202 can be temporarily joined via an attachment means 204 adjacent the first longitudinal fold line 108 present on the first base drape material and adjacent the upper edge 214 of the second base drape material 202. The attachment means 204 can be in the form of an adhesive, seam, seal, hook and loops system, or any other suitable means of joining two materials to each other. In any event, the attachment means 204 can be located on a of both the first base drape material 102 and the second base drape material 202, just the first base drape material 102, or just the second base drape material 202 so long as the attachment means 204 sufficiently joins the first base drape material 102 to the second base drape material 202. Further, when located on the first base drape material 102, the attachment means 204 can be present on the outer surface 164B of the upper section 164 of the first base drape material 102 (see FIG. 5), and when located on the second base drape material 202, the attachment means can be present on the inner surface 264A of the upper section 264 (see FIGS. 3 and 5).

Meanwhile, FIG. 5 illustrates a top perspective view of the pocket and drape system 100 of FIGS. 1-4 after supplies 130 in the first zone of pockets 104 has been used and supplies present in a second zone of pockets 106 (see FIG. 5) need to be accessed. To initiate the steps to access the second zone of pockets 106, the optional release liner 199 is first removed (see FIGS. 4-5) from the attachment means 198 adjacent the lower edge 116 of the first base drape material 101 and the first base drape material 102 is folded upwardly in the transverse or vertical direction T from the lower edge 116 towards the first longitudinal fold line 108 such that a portion of the first base drape material 102 (e.g., the lower section 166) covers the first zone of pockets 104 present on another portion of the first base drape material 102 (e.g., the upper section 164). Then, the attachment means 198, which can be in the form of an adhesive (e.g., a pressure sensitive adhesive), seal, tape, hook and loop system, or any other suitable attachment means, can be used to seal the upper section 164 and the lower section 166 of the first base drape material 102 together. Further, it is also to be understood that the optional release liner 199 and the attachment means 198 can alternatively be present adjacent the upper edge 114 of the first base drape material 102 rather than the lower edge 116.

Figure 6:
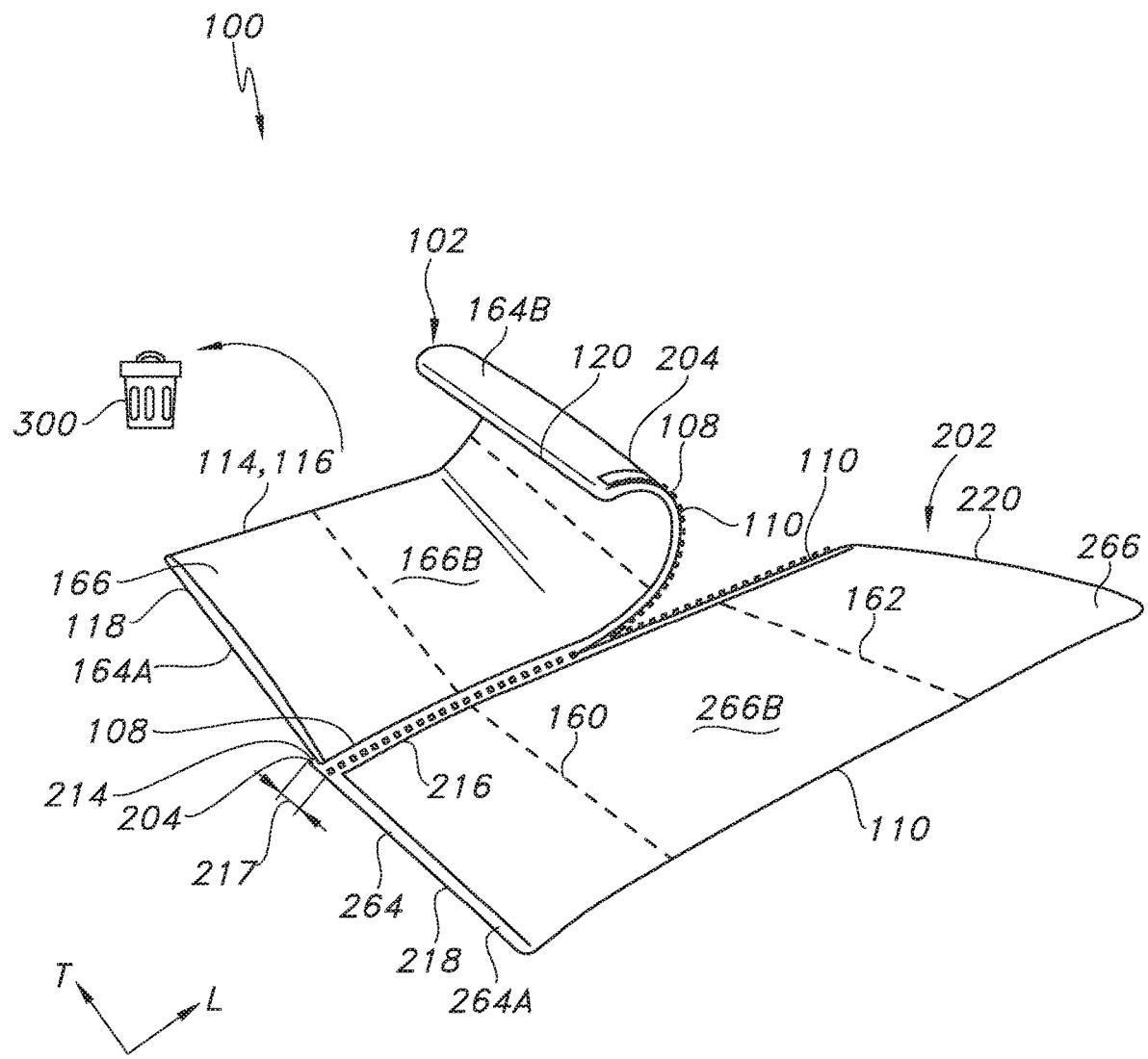
FIG. 6 illustrates a top perspective view of the pocket and drape system of FIGS. 1-5 after the first base drape material has been sealed and as the first base drape material is being separated from a second base drape material via a tearable feature, where the first base drape material can be thrown in a waste receptacle after completion of the first part of the procedure and the second base drape material can be prepared for use in a second part of the procedure.

Once the desired sections of the first base drape material 102 have been sealed together at the desired location, the first base drape material 102 can be separated from the second base drape material 202 to which it has been temporarily attached via tearable feature 210, which is shown in FIGS. 3-6. Referring specifically to FIG. 6, a user can rip or tear the system 100 along the tearable feature 210, which extends in the longitudinal direction L and is formed on the second base drape material 202 adjacent the upper edge 214. However, a distance 217 can separate the upper edge 214 and the tearable feature 210 to allow for the first base drape material 102 to be attached to the second base drape material via attachment means 204 as described above. The tearable feature 210 can be in the form of perforations or any other suitable feature that allows the first base drape material 102 to be easily separated from the second base drape material 202 after the supplies 130 in the first zone of pockets 104 have been used in a first part of a medical procedure and need to be discarded. Once the first base drape material 102 is separated from the second base drape material 202, the user can discard the first base drape material 102 in a waste receptacle 300 as shown in FIG. 6. Then, the second base drape material 202 can be prepared for use in a second part of the procedure.

Figure 7:
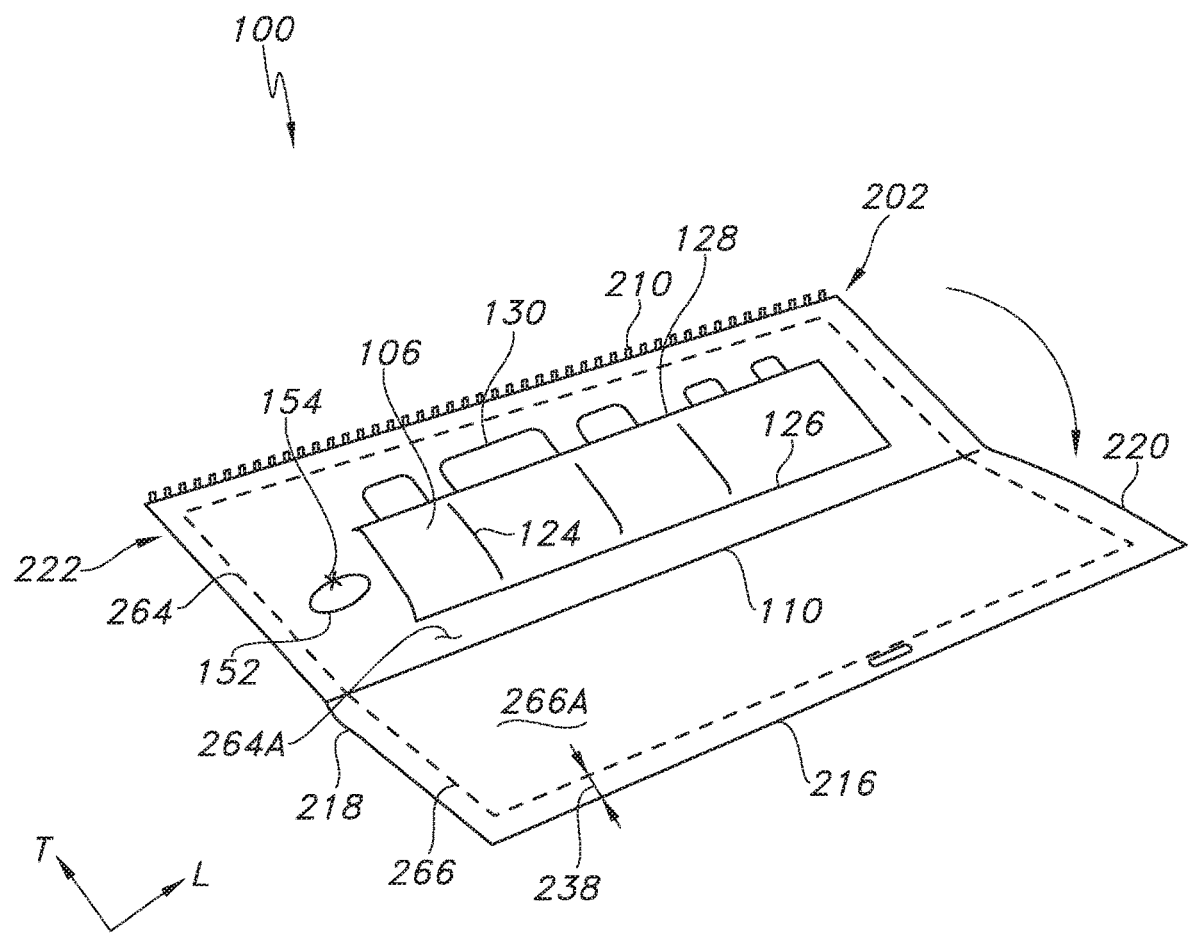
FIG. 7 illustrates a top perspective view of the pocket and drape system of FIGS. 1-6 after the second base drape material has been unfolded downwards in the transverse or vertical direction at a second longitudinal fold line to reveal a second zone of pockets present on a surface of the second base drape material that can be used in a second part of the procedure.

Specifically, and referring to FIG. 7, the second base drape material 202 can be unfolded at the second longitudinal fold line 110 by unfolding the base drape material 202 downward in the transverse or vertical direction T to reveal a second zone of pockets 106 present on the inner surface 264A of the upper section 264 of the second base drape material 202, which can contain supplies 130 to be used in a second part of a medical procedure. In FIG. 7, the second zone of pockets 106 (which can include multiple rows, not shown) is illustrated as being disposed on the inner surface 264A of the upper section 264 of the second base drape material 202, although it is to be understood that the second zone of pockets 106 can alternatively be disposed on the inner surface 266A of the lower section 266 of the second base drape material 202, or the second zone of pockets 106 can be present on both the inner surface 264A and the inner surface 266B. In any event, the second zone of pockets 106 is positioned on the second base drape material 202 such that a boundary 238 between the perimeter 222 of the first base drape material 202 as defined by upper edge 214, first side edge 218, lower edge 216, and second side edge 220 and the second zone of pockets 106 spans a distance in the longitudinal L direction and the transverse T direction of at least about 40 millimeters, such as at least about 45 millimeters, such as at least about 50 millimeters. For instance, boundary 238 between the perimeter 222 of the second base drape material 202 and the second zone of pockets 204 can span a distance ranging from about 40 millimeters to about 150 millimeters, such as from about 45 millimeters to about 125 millimeters, such as from about 50 millimeters to about 100 millimeters. Without intending to be limited by any particular theory, the present inventors have found that a boundary 238 spanning such a distance can help in maintaining the sterility of the system 100.

Turning now to the first zone of pockets 104 and the second zone of pockets 106, the one or more rows of pockets in each zone 104 and 106 can include any suitable number of individual compartments of varying sizes depending on what supplies 130 are required for any given procedure for which the system 100 is being used. For illustrative purposes only, the first zone of pockets 104 in FIG. 2 includes four individual pockets of different sizes, and the second zone of pockets 106 includes four individual pockets of different sizes, where the individual pockets are formed via a plurality of vertical seals 124 extending in the transverse or vertical direction T in each zone of pockets 104 and 106. As shown in FIGS. 4 and 7, the first zone of pockets 104 and the second zone of pockets 106 each include a sealed end 126 and a free end 128 extending in the longitudinal or horizontal direction H, whereby supplies 130 can be inserted into the individual pockets in each row via the free or unsealed end 128. Further, it is to be understood that although only one row of pockets is shown in the first zone of pockets 104 and one row of pockets is shown in the second zone of pockets 106, any suitable number of rows of pockets can be utilized so long as a sufficient boundary 138 or 238 as described above is maintained between the perimeter 122 or 222 of the first and second base drape material 102 and 202 and any additional rows of pockets. Regardless of the particular number of pockets, number of rows of pockets, and size of each individual pocket, the pockets can be formed from a clear or transparent material such that a user can easily identify the various supplies 130 contained within in each pocket. Depending on the procedure for which the system is being used, the supplies 130 can include, for example, hand sanitizer, alcohol prep pads, saline ampoules, gloves, masks, bouffant caps, surgical gowns, thermometers, measuring tape, scissors, scalpels, hemostats, syringes, tape, bandages, swabs, wipes, suture kits, skin closure tape, wound closures, antibiotic applicators or wands, antibiotic creams/gels/lotions/sprays, scalpel blades, catheters, catheter securement devices, filter straws, drapes, tourniquets, room stop signs, and the like.

Further, it is to be understood that, in some embodiments, one or more elastic loops 152 can be disposed on the first base drape material 102 (not shown) and/or the second base drape material 202 (see FIG. 7) in alignment with one or more of the zones of pockets 104 and 106. In addition, the elastic loop 152 can be secured to the first base drape material 102 and/or the second base drape material 202 via any suitable attachment means 154 such as tape, adhesive, bonding, sewing, etc.). Such an elastic loops 152 can be used to securely and snugly hold certain supplies 130 in place such as instruments that may be prone to fall out of a pocket during movement or transport of the pocket and drape system 100, which can help enhance the sterility of the pocket and drape system 100, as certain instruments may have sharp tips that could potentially create holes, cuts, or pin pricks in the first base drape material 102 and/or the second base drape material 202 were such instruments to fall out of a pocket.

In general, the arrangement and manner of unfolding the pocket and drape system 100 described above allows a user to first access the supplies 130 contained in the first zone of pockets 104 in a sterile condition. Then, after the user is finished with or no longer needs the supplies 130 contained in the first zone of pockets 104, the user can access supplies 130 contained in the second zone of pockets 106, which were maintained in a sterile condition when the supplies 130 in the first zone of pockets 104 were being used based on the particular longitudinal and transverse folding arrangement of the pocket and drape system 100 of the present invention, as well as the particular arrangement of the first base drape material 102 and the second base drape material 202 with respect to each other.

The construction of the pocket and drape system 100 described above can be carried out as follows. First, the first base drape material 102 and the second base drape material 202 can be cut to the appropriate size depending on the intended use of the pocket and drape system 100. Then, the clear or transparent material used to form one or more rows defining the first zone of pockets 104 and the second zone of pockets 106, which can likewise include one or more rows, can be attached to the desired section of the first base drape material 102 (e.g., the inner surface 164A of the upper section 164) and the second base drape material 202 (e.g., the inner surface 264A of the upper section 264) using any suitable attachment or sealing method. In one particular embodiment, the first zone of pockets 104 and the second zone of pockets 106 can be attached to the desired section of the first base drape material 102 and the second base drape material 202, respectively, via heat sealing. However, other sealing methods can be used and include, but are not limited to, the use of a pressure sensitive adhesive, ultrasonic bonding, double sided tape, etc. Further, vertical seals 124 can be formed in the first zone of pockets 104 and the second zone of pockets 106 via any suitable method such as via heat sealing, sewing a seam, etc. Each pocket size can vary based on the specifications necessary for the intended use and for the contents to be contained therein.

In use, the pocket and drape system 100 is used to hold specific supplies 130 necessary for any number of medical or veterinary procedures, or any other procedure where a sterile environment is required. For instance, the pocket and drape system 100 can be used during port access dressing changes, dialysis dressing changes, peripherally inserted central catheter (PICC) dressing changes, central venous catheter (CVC) dressing changes, PICC insertion procedures, Foley catheter insertion procedures, peripheral IV placement procedures, laceration repair procedures, etc., where the supplies needed to carry out such procedures are contained in the pocket and drape system 100 described herein. For instance, a portion of the supplies 130 can be present in the first zone of pockets 104, which are sterile upon opening of the system and are accessed by unfolding the first base drape material 102 in the transverse or vertical direction T at the first longitudinal fold line 108 to reveal a sterile portion (e.g., the inner surface 164A of the upper portion 164 and the inner surface 166A of the lower portion 166) of the first base drape material 102. Once the supplies 130 in the first zone of pockets 104 are depleted and/or no longer needed, the first base drape material 202 can be sealed and removed from the second base drape material 202, after which the second base drape material 202 can be unfolded in the transverse or vertical direction T at the second longitudinal fold line 110 to expose the supplies 130 inserted into the second zone of pockets 106 located on the second base drape material 202, which can also be utilized in during the procedure. The particular order and arrangement of the folds made in the first base drape material 102 and the second base drape material 202 and the manner in which the first base drape material 102 and the second base drape material 202 are joined to each other temporarily allows for the creation of at least two sterile zones for use during a multi-step procedure.

Turning now to the particular manner in which the first longitudinal fold line 108, the second longitudinal fold line 110, the first transverse fold line 160, the second transverse fold line 162, and any other fold lines are formed, it is to be understood that, in some embodiments, the fold lines may be predetermined in that fold lines are physically formed on the first base drape material 102 and the second base drape material 202 to indicate to the user exactly where the first base drape material 102 and the second base drape material 202 should be folded to arrive at the system 100 of the present invention. For instance, each of the fold lines may be in the form of a seam (or seams) such as, for example, a stitched seam, an ultrasonic bond seam, an adhesive bond seam, a thermo-mechanical bond seam (e.g., a bar seal seam) or combinations thereof, where such seams can result from joining layers or plies together to form the first base drape material 102 and the second base drape material 202. Alternatively and/or additionally, the fold lines may be identified by pre-made creases formed in the first base drape material 102 or the second base drape material 202, by printing of lines on the first base drape material 102 and the second base drape material 202, or by imprinting a thermo-mechanical bond line (e.g., bar seal bond line) or pattern or other indicia on the first base drape material 102 and the second base drape material 202. Further, it is to be understood that the fold lines may be in the form of intermittent lines or indicia and may be provided directly on the first base drape material 102 and the second base drape material 202. However, in other embodiments, instructions could direct a user where to form the fold lines during assembly and wrapping of the system 100 such that it is not required that the fold lines described above be predetermined.

The method for folding, sterilizing, and then unfolding the pocket and drape system 100 of the present invention will now be described in detail. First, the base drape material 102 can be cut to the desired size to define an upper edge 114, a lower edge 116, a first side edge 118, and a second side edge 120 to define a perimeter 122, and the second base drape material 202 can be cut to the desired size to define an upper edge 214, a lower edge 216, a first side edge 218, and a second side edge 220 to define a perimeter 222. In addition, one or more predetermined longitudinal or horizontal fold lines 108 can be formed on the first base drape material 102 to divide the first base drape material 102 into an upper section 164 and a lower section 116, and one or more predetermined longitudinal or horizontal fold lines 110 can be formed on the second base drape material 202 to divide the second base drape material 202 into an upper section 264 and a lower section 266, although it is also to be understood that the fold lines may not be formed until the first base drape material 102 and the second base drape material 202 are folded prior to sterilization.

Next, the first zone of pockets 104 and the second zone of pockets 106 can be attached to the first base drape material 102 (e.g., on the inner surface 164A of the upper section 164) and the second base drape material 222 (e.g., on the inner surface 264A of the upper section), respectively, using any suitable attachment or sealing method. Further, any number of rows of pockets and any number of individual pockets, as well as one or more elastic loops 152 attached via attachment means 154, can be present on any of the sections described above, except for the outer surface 264B of the upper section 264 of the second base drape material 202, as this section forms the exterior surface of the system 100 after it is sterilized and thus would not be considered sterile after sterilization and removal from a sterilization pouch or wrap if present. Regardless of the number of rows of pockets or individual pockets present in each row in the first zone of pockets 104 and the second zone of pockets 106, a sealed end 126 can be formed in the longitudinal or horizontal direction L via any suitable sealing method, and vertical seals 124 can also be formed in the transverse or vertical direction T via any suitable sealing method to define form individual pockets that define a free end 128 present in the longitudinal or horizontal direction L of the zones of pockets 104 and 106. Once the individual pockets are formed and once any optional elastic loops 152 are attached, supplies 130 can be inserted into the pockets of the first zone of pockets 104 and the second zone of pockets 106 via the free end 128.

Then, after the desired supplies 130 are loaded into the first zone of pockets 104 and the second zone of pocket 106, the desired longitudinal fold lines can be created in the first base drape material 102 and the second base drape material 202. Further, while the first longitudinal fold line 108 can be formed in the first base drape material 102 by folding it in half such that the lower edge 116 is aligned with and positioned above the upper edge 214, the second longitudinal fold line 110 can be formed in the second base drape material 202 such that a distance 217 exists between the lower edge 216 and the upper edge 214 to allow for the attachment of the first base drape material 102 to the second base drape material 202 via attachment means 204 and to allow for the tearable feature 210 to be present on the second base drape material 202.

Next, once the longitudinal fold lines 108 and 110 are made, the first base drape material 102 and the second base drape material 202 can be temporarily joined to each other at attachment means 204 present on the second base drape material 202 within the distance 216 between the lower edge 216 and the upper edge 214, adjacent the first longitudinal fold line 108 on the outer surface 164B of the upper section 164 of the first base drape material 102, or both. Thus, the first base drape material 102 and the second base drape material 202 are attached at the general location of the first longitudinal fold line 108 of the first base drape material 102 and the upper edge 214 of the second base drape material 202. Further, the tearable feature 210 can also be formed on the second base drape material 202 on the inner surface 264A of the upper section 264 of the second base drape material in the distance 217 between the lower edge 216 and the upper edge 214 of the folded second base drape material 202. In some embodiments, it is to be understood that the tearable feature 210 can be aligned with the attachment means 204 and that the tearable feature 210 can be formed at the same time that that first base drape material 102 and the second base drape material 202 are adhered to each other, such as via pressure bonding, sealing, etc.

After the first base drape material 102 and the second base drape material 202 are joined as described above, the upper edge 114 and lower edge 116 of the first base drape material 102 can be folded downward together in the transverse or vertical direction T towards the second longitudinal fold line 110 so that the upper edge 114 and lower edge 116 of the first base drape material 102 are positioned above the second longitudinal fold line 110, resulting in a top perspective view as shown in FIG. 3. Then, the system can be folded in the longitudinal or horizontal direction L at the first transverse fold line 160 (e.g., to the right) followed by the second transverse fold line 162 in the opposite direction (e.g., to the left), after which the system can be sealed with an attachment means 136. Then, the system 100 can be sterilized and stored until ready for use in a multi-step procedure. After sterilization and once the system 100 is needed during a particular medical procedure, the system 100 can be unfolded as set forth in FIGS. 1-7 as described in detail above.

The following examples serve to illustrate the various uses of the claimed invention in actual practice in the medical field.

Example 1—Port Access Dressing Change

The following steps can be performed when utilizing the pocket and drape system of the present invention when changing port access dressing.
1. Assess patient for CHG and/or TEGADERM™ allergy.
2. Determine if patient needs a power injectable needle.
3. Gather appropriate supplies including the pocket and drape system 100 of the present invention, including a correct size noncoring safety needle, correct size sterile gloves, and needleless connectors.
4. Explain procedure to patient.
5. Clean surface to be used to hold the pocket and drape system 100 of the present invention with germicidal wipe (e.g., overbed table).
6. Retrieve the pocket and drape system 100 and remove the system 100 from its sterilization packaging or other packaging (if present) on a cleaned surface.
7. Don mask and place mask on patient.
8. Perform hand hygiene with antiseptic hand cleanser.
9. Don clean gloves.
10. Open the pocket and drape system 100 by unfolding the system 100 longitudinally (e.g., in the longitudinal or horizontal direction L), in the direction indicated by directional indicia 134, if present, at the second transverse fold line 162 (e.g., to the right) after unfastening the attachment means (safety seal) 136 if present, and then unfold the pocket and drape system 100 longitudinally in the opposite direction (e.g., to the left) at the first transverse fold line 160, followed by unfolding the first base drape material 102 upward at the first longitudinal fold line 108 to expose the first zone of pockets 104 present on the first base drape material 102.
11. Disconnect any infusions.
12. Scrub the needleless connector with alcohol prep pad for at least 15 seconds and allow to dry completely. If removing CUROS™ or a similar port protector, ensure it has been in place for a minimum of 1 minute.
13. Attach saline flush syringe to needleless connector maintaining sterility after removing protective cap from distal end of syringe.
14. Verify blood return.
15. Flush lumen with 10 milliliter sterile syringe using vigorous pulsatile technique to clear lumen (flush with heparin solution as prescribed if not reaccessing device). Leave 0.5 millimeter in syringe before detaching (do not bottom out syringe).
16. Remove dressing and discard.
17. Grasp needle with dominant hand while supporting the vascular access device with non-dominant hand, utilizing safety mechanism of needle.
18. Pull needle straight up and out of vascular access device and discard in sharps container.
19. Assess site for signs of infection or drainage. If not reaccessing, apply bandage over insertion site.
20. Remove and discard gloves. Set aside second set of sterile gloves and hand sanitizer gel packet.
21. Perform hand hygiene with antiseptic hand cleaner.
22. Don sterile gloves.
23. Aseptically reveal the second zone of pockets 106 present on the second base drape material 202 by folding the first base drape material 102 upward in the transverse or vertical direction T from its lower edge 116 towards the first longitudinal fold line 108, removing the first base drape material 102 from the second base drape material 202, and unfolding the second base drape material 202 downward in the transverse or vertical direction T at the second longitudinal fold line 110 by bringing the lower edge 216 of the second base drape material 202 towards the second longitudinal fold line 110.
24. Drop noncoring needle and sterile saline into sterile field.
25. Activate CHG wand and cleanse skin with solution using a back and forth motion for 30 seconds. Allow CHG to completely dry.

26. Attach sterile saline syringe to needleless connector(s) and prime. Attach primed needleless connector(s) to noncoring needle and prime. Leave syringe attached.
27. Open CHG gel pad.
28. Apply sterile drape, absorbent side up, adjacent to insertion site.
29. Apply skin protectant and allow to dry. Never apply skin protectant under CHG gel pad.
30. Stabilize port with non-dominant hand and insert noncoring needle perpendicular to the skin, advancing until needle contacts port base.
31. Verify blood return.
32. Flush lumen with 10 milliliter syringe using vigorous pulsatile technique to clear lumen (flush with heparin solution as prescribed if not reaccessing device). Leave 0.5 millimeter in syringe before detaching (do not bottom out syringe).
33. Position CHG gel pad around needle.
34. Apply dressing: shirt—apply dressing to cover the insertion site; pants—apply pre-cut securement tape strip under the extension legs and over the dressing border; belt—apply dressing label with date, time, gauge, length, if powerport and initials.
35. Secure extension tubing with tape.
36. Discard supplies. Remove gloves and masks. Perform hand hygiene.
37. Document procedure in patient record. Notify charge nurse if early dressing change.

Example 2—Dialysis Dressing Change

The following steps can be performed when utilizing the pocket and drape system of the present invention when changing a dialysis dressing.
1. Assess patient for CHG and/or TEGADERM™ allergy.
2. Gather appropriate supplies including the pocket and drape system 100, including a central line dressing kit and correct size sterile gloves.
3. Explain procedure to the patient.
4. Clean surface to be used to hold the pocket and drape system 100 with germicidal wipe (e.g., overbed table).
5. Retrieve the pocket and drape system 100 and remove the system 100 from its sterilization packaging or other packaging (if present) on a cleaned surface.
6. Don mask and place mask on patient.
7. Perform hand hygiene with antiseptic hand cleanser.
8. Don clean gloves.
9. Open the pocket and drape system 100 as described above in Example 1 to expose the first zone of pockets 104 present on first base drape material 102.
10. Apply drape, absorbent side up, adjacent to insertion site.
11. Measure external length of catheter from insertion site to zero mark.
12. Remove dressing by pulling towards insertion site. If needed, use alcohol prep pads to loosen dressing edges. If needed, apply tape strips to stabilize tubing. If CHG gel pad has adhered to catheter add 1-2 gtts sterile saline to gel paid, wait until absorbed. CHG should release. Repeat until CHG is no longer adherent.
13. Assess site for signs of infection or drainage.
14. Remove and discard gloves. Set aside second set of sterile gloves and hand sanitizer gel packet.
15. Perform hand hygiene with antiseptic hand cleanser.
16. Don sterile gloves.
17. Open the pocket and drape system 100 aseptically as described above in Example 1 to reveal the second zone of pockets 106 present on the second base drape material 202.
18. Grasp catheter lumens with sterile 4×4 gauze and hold away from patient's skin.
19. Use alcohol swab sticks to remove dried blood at insertion site, if applicable, and allow to dry completely.
20. Activate CHG wand and cleanse skin with solution using a back and forth motion for 30 seconds. Allow CHG to completely dry.
21. Apply skin protectant and allow to dry. Never apply skin protectant under CHG gel pad.
22. Center CHG gel pad over insertion site before laying dressing down.
23. Apply dressing: shirt—apply dressing to cover the insertion site; pants—apply pre-cut securement tape strip under the extension legs and over the dressing border; belt—apply dressing label with date, time, and initials.
24. Discard supplies. Remove gloves and masks. Perform hand hygiene.
25. Document procedure in patient record. Notify charge nurse if early dressing change. Document external length of catheter in EHR and compare to previous measurement.

Example 3—PICC Dressing Change

The following steps can be performed when utilizing the pocket and drape system of the present invention when changing a PICC dressing.
1. Assess patient for CHG and/or TEGADERM™ allergy.
2. Gather appropriate supplies including the pocket and drape system 100, including a central line dressing kit and correct size sterile gloves.
3. Explain procedure to the patient.
4. Clean surface to be used to hold the pocket and drape system 100 with germicidal wipe (e.g., overbed table).
5. Retrieve the pocket and drape system 100 and remove the system 100 from its sterilization packaging or other packaging (if present) on a cleaned surface.
6. Don mask and place mask on patient.
7. Perform hand hygiene with antiseptic hand cleanser.
8. Don clean gloves.
9. Open the pocket and drape system 100 as described above in Example 1 to expose the first zone of pockets 104 present on first base drape material 102.
10. Apply drape, absorbent side up, adjacent to insertion site. 11. Measure external length of catheter from insertion site to zero mark.
12. Remove dressing by pulling towards insertion site. If needed, use alcohol prep pads to loosen dressing edges. If needed, apply tape strips to stabilize tubing. If CHG gel pad has adhered to catheter add 1-2 gtts sterile saline to gel paid, wait until absorbed. CHG should release. Repeat until CHG is no longer adherent.
13. Remove STATLOCK™ or other stabilization device with alcohol prep pad to release adhesive. Secure catheter with tape strips if needed.
14. Assess site for signs of infection or drainage.
15. Remove and discard gloves. Set aside second set of sterile gloves and hand sanitizer gel packet.
16. Perform hand hygiene with antiseptic hand cleanser.
17. Don sterile gloves.

18. Open the pocket and drape system 100 aseptically as described above in Example 1 to reveal the second zone of pockets 106 present on the second base drape material 202.
19. Grasp catheter lumens with sterile 4×4 gauze and hold away from patient's skin.
20. Use alcohol swab sticks to remove dried blood at insertion site, if applicable, and allow to dry completely.
21. Activate CHG wand and cleanse skin with solution using a back and forth motion for 30 seconds. Allow CHG to completely dry.
22. Open STATLOCK™ package.
23. Apply skin protectant to area larger than anchor pad of STATLOCK™ and allow to dry. Never apply skin protectant under CHG gel pad.
24. Apply STATLOCK™ device (closing wings/doors over PICC anchor sites) and adhere STATLOCK™ to patient skin ("click it before you stick it").
25. Apply dressing: shirt—apply dressing to cover the insertion site; pants—apply pre-cut securement tape strip under the extension legs and over the dressing border; belt—apply dressing label with date, time, and initials.
26. Discard supplies. Remove gloves and masks. Perform hand hygiene.
27. Document procedure in patient record. Notify charge nurse if early dressing change. Document external length of catheter in EHR and compare to previous measurement.

Example 4—CVC Dressing Change

The following steps can be performed when utilizing the pocket and drape system of the present invention when changing a CVC dressing.
1. Assess patient for CHG and/or TEGADERM™ allergy.
2. Gather appropriate supplies including the pocket and drape system 100, including a central line dressing kit and correct size sterile gloves.
3. Explain procedure to the patient.
4. Clean surface to be used to hold the pocket and drape system 100 with germicidal wipe (e.g., overbed table).
5. Retrieve the pocket and drape system 100 and remove the system 100 from its sterilization packaging or other packaging (if present) on a cleaned surface.
6. Don mask and place mask on patient.
7. Perform hand hygiene with antiseptic hand cleanser.
8. Don clean gloves.
9. Open the pocket and drape system 100 as described above in Example 1 to expose the first zone of pockets 104 present on first base drape material 102.
10. Apply drape, absorbent side up, adjacent to insertion site.
11. Measure external length of catheter from insertion site to zero mark.
12. Remove dressing by pulling towards insertion site. If needed, use alcohol prep pads to loosen dressing edges. If needed, apply tape strips to stabilize tubing. If CHG gel pad has adhered to catheter add 1-2 gtts sterile saline to gel paid, wait until absorbed. CHG should release. Repeat until CHG is no longer adherent.
13. Assess site for signs of infection or drainage.
14. Remove and discard gloves. Set aside second set of sterile gloves and hand sanitizer gel packet.
15. Perform hand hygiene with antiseptic hand cleanser.
16. Don sterile gloves. 17. Open the pocket and drape system 100 aseptically as described above in Example 1 to reveal the second zone of pockets 106 present on the second base drape material 202.
18. Grasp catheter lumens with sterile 4×4 gauze and hold away from patient's skin.
19. Use alcohol swab sticks to remove dried blood at insertion site, if applicable, and allow to dry completely.
20. Activate CHG wand and cleanse skin with solution using a back and forth motion for 30 seconds. Allow CHG to completely dry.
21. Apply skin protectant and allow to dry. Never apply skin protectant under the CHG gel pad.
22. Center CHG gel pad over insertion site before laying dressing down.
23. Apply dressing: shirt—apply dressing to cover the insertion site; pants—apply pre-cut securement tape strip under the extension legs and over the dressing border; belt—apply dressing label with date, time, and initials.
24. Discard supplies. Remove gloves and masks. Perform hand hygiene.
25. Document procedure in patient record. Notify charge nurse if early dressing change. Document external length of catheter in EHR and compare to previous measurement.

Example 5—PICC Insertion

The following steps can be performed when utilizing the pocket and drape system of the present invention to insert a PICC.
1. If performing procedure at the bedside, place a STOP sign on the patient room door.
2. Open the pocket and drape system 100 as described above in Example 1 to expose the first zone of pockets 104 present on first base drape material 102.
3. Identify vein and insertion site. Apply tourniquet above the anticipated insertion site. Once the vein is selected, release tourniquet but keep it in place for insertion.
4. Utilize measuring tape to measure from the planned insertion site over to the sternal notch, then down to the third intercostal space.
5. Place the patient in a supine position, extending the arm away from the body.
6. Preflush the catheter.
7. Open and drop the catheter and any additional items onto the sterile field.
8. Reapply tourniquet and tighten to assess vein under ultrasound.
9. Don mask.
10. Scrub hands and don sterile gown and gloves.
11. Prep selected site with antiseptic solution. Allow to dry. Prep site from distal portion of arm to below the antecubital area. Prep around the entire circumference of arm.
12. Drape patient with full body drape, leaving area of intended insertion exposed through the drape fenestration.
13. Inject 2% lidocaine without epinephrine intradermal at intended insertion site using a small gauge needle (25 gauge).
14. Access desired vein with the appropriate IV Catheter needle using ultrasound.

15. Place the guide wire. Gently advance the guide wire through the needle/IV catheter into vessel. At no time should the wire be forced if resistance is met. Remove the needle/IV catheter, leaving the wire in place, with 4-5" of the wire exposed. Release the tourniquet at this point.
16. Enlarge the insertion site using the #11 scalpel blade to allow the introducer to easily pass through the skin.
17. Gently insert the dilator and peel apart introducer over the guide wire, making sure the guide wire is always visible at the proximal end of the introducer. If unable to advance the dilator/introducer together, first use the dilator to enlarge the area before the introducer is added.
18. Place the wire in the desired position under fluoroscopy. Remove and measure the wire then cut the catheter to the desired length utilizing scissors (less 3 cm).
19. Remove the dilator and guide wire. Apply the non-dominant thumb over the opening of the introducer to reduce blood spillage.
20. Insert the tip of the catheter into the introducer; gently advance approximately 8-10 inches.
21. Instruct the patient turn his/her head toward the cannulated arm and tuck chin onto clavicle; gently advance the rest of the catheter into the SVC, as determined under fluoroscopy. Encourage the patient to hold his/her breath or use the Valsalva maneuver to encourage the catheter downward into the SVC.
22. Once catheter is in the correct position, peel apart the introducer and remove introducer.
23. Remove the guide wire, if applicable. Immediately clamp the catheter to prevent ingress of air.
24. Attach the syringe containing heparinized saline. Open the clamp and pull back to assess for blood return. If positive, flush the catheter with 3-5 mL heparinized saline and close the clamp. Place the cap on the catheter.
25. Secure the catheter in place utilizing securement device. Suture the catheter in place using local anesthetic as indicated. (See suturing procedure).
26. Open the pocket and drape system 100 aseptically as described above in Example 1 to reveal the second zone of pockets 106 present on the second base drape material 202.
27. Cleanse the site with alcohol swabs. Allow to dry.
28. Cover with a sterile dressing and wound closure strips.
29. Attach needleless connectors to the catheter lumens.
30. Utilize surgical tape to secure catheter lumens in place.
31. Have a physician/radiologist confirm the catheter tip placement. Do not use the catheter until placement has been confirmed.

TABLE 1

Location of Supplies Contained in Pocket and Drape System for PICC Insertion and Their Location

| Supplies Contained within Drape System on Top of 1$^{st}$ Zone of Pockets | Supplies Contained in 1$^{st}$ Zone of Pockets | Supplies Contained in 2$^{nd}$ Zone of Pockets |
|---|---|---|
| Room Stop Sign | Sterile Gloves | Alcohol Swab |
| Tourniquet | Scalpel | Transparent Dressing |
| Measuring Tape | IV Catheter, 20 G | Wound Closures (3) |
| Fenestration Drape | Hypodermic safety needle | Surgical tape |
| Surgical Gown | Filter straw | Needleless valve end caps (2) |
| Bouffant Cap | Towel, absorbent | Catheter Securement Device |
| Masks | Syringes | |
| Sterile Gloves | Lidocaine | |
| Hand Sanitizer Gel | Saline | |
| Chloraprep | Scissors | |
| | Gauze 4 × 4 | |
| | Gauze 2 × 2 | |
| Other Supplies | | |
| PICC Catheter w/guidewire | | |
| Microintroducer | | |
| Introducer needle | | |

Example 6—Foley Catheter Insertion

The following steps can be performed when utilizing the pocket and drape system of the present invention to insert a Foley catheter.
1. Verify Foley catheter order.
2. Review record for allergies (e.g., latex and iodine).
3. Explain procedure to patient.
4. Gather supplies including the pocket and drape system 100.
5. Open the pocket and drape system 100 as described above in Example 1 to expose the first zone of pockets 104 present on first base drape material 102.
6. Wash hands.
7. Don clean gloves.
8. Ensure proper patient positioning: female—supine position with knees flexed and separated with feet flat on bed; male—supine with legs extended.
9. Cleanse the perineal area with soap and water; dry.
10. Prepare area for sterile field.
11. Drop drainage bag within the sterile field.
12. Drape patient with drapes supplied in the system 100.
13. Open the pocket and drape system 100 aseptically as described above in Example 1 to reveal the second zone of pockets 106 present on the second base drape material 202.
14. Don sterile gloves.
15. Saturate cotton balls with iodine solution.
16. Open packet of lubricant and lubricate catheter tip.
17. Examine drainage bag and ensure drain is closed.
18. Prepare insertion site sterilely: female—separate the labia with non-dominant hand and keep opening during entire cleaning process, with dominant hand, cleanse with iodine-soaked cotton balls, using a single downward motion, outer edges first, then the center, over the meatus itself, maintaining separation of labia; male—if the patient is uncircumcised, retract the foreskin before cleansing, hold the penis with non-dominant hand, stretching to a 60-90° C. angle, with dominant hand, cleanse with iodine-soaked cotton balls, using a circular motion, staring at the meatus and working outward, using 1 cotton ball for each circle.
19. With dominant hand, while holding the remainder of the catheter so that it does not touch anything but a sterile field, grasp the end of the catheter near the tip.
20. Insert the catheter into the urinary meatus until urine is returned.
21. Stop advancement if resistance is met and notify physician.
22. Attach the saline filled syringe to balloon port and inflate the balloon of the indwelling catheter.
23. Attach catheter to drainage bag.
24. Hang bag below bladder level.
25. Secure catheter drainage tubing to the patient's thigh with leg band and
Velcro closure.
26. Remove supplies and disposed of per facility policy.
27. Change gloves and don clean gloves.
28. Clean perineal area with soap and water.
29. If male's foreskin has been retracted, replace it.
30. Cover patient to restore privacy.
31. Remove gloves and wash hands.
32. Document procedure and amount, color, and clarity of urine.

TABLE 2

Supplies Contained in Pocket and Drape System for Foley Catheter Insertion and Their Location

| Other Supplies | Supplies Contained in 1$^{st}$ Zone of Pockets | Supplies Contained in 2$^{nd}$ Zone of Pockets |
|---|---|---|
| Drainage bag | Clean gloves<br>Fenestrated drape<br>Lower small sheet or chuck | Sterile gloves<br>Cotton balls<br>Iodine packet<br>Catheter<br>Lubricant packet<br>Saline filled syringe<br>Leg band<br>Clean up cloth |

Example 7—Peripheral IV Placement

The following steps can be performed when utilizing the pocket and drape system of the present invention to insert a peripheral IV.
1. Gather all the supplies and equipment needed, including the pocket and drape system 100.
2. Wash hands and don clean gloves.
3. Open the pocket and drape system 100 as described above in Example 1 to expose the first zone of pockets 104 present on first base drape material 102.
4. Place tourniquet around the patient's arm to enhance site visualization
5. Prep selected site with antiseptic solution. Allow to dry.
6. Open the pocket and drape system 100 aseptically as described above in Example 1 to reveal the second zone of pockets 106 present on the second base drape material 202.
7. Don sterile gloves.
8. Insert catheter utilizing proper technique.
9. Position the catheter.
10. Hold catheter with thumb of non-dominant hand and remove needle.
11. Attach extension tubing to the catheter hub.
12. Release tourniquet.
13. Secure catheter with securement device.
14. Cover the insertion site with a dressing.
15. Make sure the extension tubing contains a needle-less connector or attach a needle-less connector as needed.
16. Secure the extension tubing with tape.
17. Label per policy with date, time and initials.
18. Flush the catheter with regular saline solution as indicated.
19. Remove gloves and wash hands.

TABLE 3

Supplies Contained in Pocket and Drape System for Peripheral IV Placement and Their Location

| Other Supplies | Supplies Contained in 1$^{st}$ Zone of Pockets | Supplied Contained in 2$^{nd}$ Zone of Pockets |
|---|---|---|
| IV Catheter<br>Gauze<br>Transparent Dressing<br>Flush Syringe 10 ml | Sterile Gloves<br>Tourniquet<br>Antiseptic | Sterile Gloves<br>Catheter<br>Dressing<br>Securement Device<br>Tape Roll<br>Extension Set with Valve<br>Label |

Example 8—Laceration Repair

1. Don clean gloves and retrieve pocket and drape system 100.
2. Open the pocket and drape system 100 as described above in Example 1 to expose the first zone of pockets 104 present on first base drape material 102.
3. Don a new pair of clean gloves and mask.
4. Apply betadine or chlorhexidine gluconate (CHG) solution to the affected wound area.
5. Inject lidocaine if needed.
6. Mix saline and betadine solutions to prepare for wound cleaning, as appropriate. Utilize medicine cups for mixing.
7. Inspect wound and flush would with normal saline or a betadine/saline mixture, utilizing the large flush syringe, per hospital protocol.
8. Open the pocket and drape system 100 aseptically as described above in Example 1 to reveal the second zone of pockets 106 present on the second base drape material 202.
9. Don sterile gloves.
10. Apply fenestrated drape to the wound.
11. Suture the wound applying the appropriate amount of sutures. Utilize needle holder, forceps and scissors to perform the suturing.
12. Remove fenestrated drape.
13. Wipe off antiseptic solution using clean gauze and saline.
14. Dress per policy, remove gloves and wash hands.

TABLE 4

| Supplies Contained in Pocket and Drape System for Laceration Repair and Their Location | | |
|---|---|---|
| Other Supplies | Supplies Contained in $1^{st}$ Zone of Pockets | Supplied Contained in $2^{nd}$ Zone of Pockets |
| Filter Straw | Clean Gloves | Sterile Gloves |
| Betadine Solution | Mask w/Face Shield | Fenestrated Drape |
| Saline Solution | Lidocaine | Instrument: Needle Holder |
| | Syringes w/Luer Lock | Instrument: Scissors |
| | Medicine Cups | Instrument: Hemostat |
| | Needle 18G × 1.5" | Instrument: Forceps |
| | Needle 25G × 0.625" | Towel |
| | Needle 27G × 1.5" | Gauze 4 × 4 |
| | Betadine or CHG Solution | Gauze 2 × 2 |
| | Large Flush Syringe | |

While the invention has been described with reference to certain exemplary embodiments thereof, those skilled in the art may make various modifications to the described embodiments without departing from the scope of the invention. The terms and descriptions used herein are set forth by way of illustration only and not meant as limitations. In particular, although the present invention has been described by way of examples, a variety of compositions and processes would practice the inventive concepts described herein. Although the invention has been described and disclosed in various terms and certain embodiments, the scope of the invention is not intended to be, nor should it be deemed to be, limited thereby and such other modifications or embodiments as may be suggested by the teachings herein are particularly reserved, especially as they fall within the breadth and scope of the claims here appended. Those skilled in the art will recognize that these and other variations are possible within the scope of the invention as defined in the following claims and their equivalents.

What is claimed is:

1. A pocket and drape system comprising:
    a first base drape material having an upper edge and a lower edge both extending in a longitudinal direction and a first side edge and a second side edge both extending in a transverse direction to define a perimeter, wherein the first base drape material includes a first longitudinal fold line;
    a second base drape material having an upper edge and a lower edge both extending in a longitudinal direction and a first side edge and a second side edge both extending in a transverse direction to define a perimeter, wherein the second base drape material includes a second longitudinal fold line;
    a first zone of pockets located on a surface of the first base drape material, wherein the first longitudinal fold line divides the first base drape material into an upper section and a lower section each having an inner surface and an outer surface, wherein the first zone of pockets is present on the inner surface of the upper section, the inner surface of the lower section, or both; and
    a second zone of pockets located on a surface of the second base drape material:
    wherein a portion of the first base drape material adjacent the first longitudinal fold line is temporarily joined to a portion of the second based drape material adjacent the upper edge of the second base drape material, and wherein a first transverse fold line and a second transverse fold line extend from the upper edge of the first base drape material to the lower edge of the second base drape material.

2. The pocket and drape system according to claim 1, wherein the first zone of pockets and the second zone of pockets are formed from a clear material.

3. The pocket and drape system according to claim 1, wherein a plurality of vertical seals are present in the first zone of pockets and the second zone of pockets to define individual pockets in each of the first zone of pockets and the second zone of pockets.

4. The pocket and drape system according to claim 1, wherein the first zone of pockets and the second zone of pockets each include a free end and a sealed end.

5. The pocket and drape system according to claim 1, wherein the inner surface of the upper section, the inner surface of the lower section, or both include an attachment means to adhere the inner surface of the upper section to the inner surface of the lower section.

6. The pocket and drape system according to claim 1, wherein the second longitudinal fold line divides the second base drape material into an upper section and a lower section each having an inner surface and an outer surface, wherein the second zone of pockets is present on the inner surface of the upper section, the inner surface of the lower section, or both.

7. The pocket and drape system according to claim 1, wherein the first base drape material and the second drape material are separable from each other via a tearable feature extending in the longitudinal direction adjacent the first longitudinal fold line and the upper edge of the second base drape material.

8. The pocket and drape system according to claim 1, wherein a boundary exists between the perimeter of the first base drape material and the first zone of pockets, the second based drape material and the second zone of pockets, or both.

9. The pocket and drape system according to claim 8, wherein the boundary spans a distance ranging from about 40 millimeters to about 150 millimeters.

10. The pocket and drape system according to claim 1, wherein the first base drape material, the second base drape material, or both is formed from a sterilization material.

11. The pocket and drape system according to claim 1, wherein the first zone of pockets and the second zone of pockets contain instruments, medical supplies, or a combination thereof for use in a multi-step sequential procedure.

12. The pocket and drape system according to claim 11, wherein the multi-step sequential procedure is selected from procedures for abdominal aortic aneurysm repair; limb amputation; appendix surgery; AV shunt for dialysis; bile duct, liver, or pancreatic surgery; breast surgery; cardiac surgery; coronary bypass with chest and donor incisions; coronary bypass graft; carotid endarterectomy; gallbladder surgery; colon surgery; craniotomy; cesarean section; spinal fusion; open reduction of fracture; gastric surgery; herniorrhaphy; hip prosthesis; heart transplant; abdominal hysterectomy; knee prosthesis; kidney transplant; laminectomy; liver transplant; neck surgery; kidney surgery; ovarian surgery; pacemaker surgery; prostate surgery; peripheral vascular bypass surgery; rectal surgery; small bowel surgery; spleen surgery; thoracic surgery; thyroid and/or parathyroid surgery; vaginal hysterectomy; ventricular shunt; and exploratory laparotomy.

13. A method for maintaining a sterile field while performing a multi-step sequential procedure, the method comprising the steps of:
providing a pocket and drape system including a first base drape material having an upper edge and a lower edge both extending in a longitudinal direction and a first side edge and a second side edge both extending in a transverse direction to define a perimeter, wherein the first base drape material includes a first longitudinal fold line, wherein a first zone of pockets is located on a surface of the first base drape material, wherein the first longitudinal fold line divides the first base drape material into an upper section and a lower section each having an inner surface and an outer surface, wherein the first zone of pockets is present on the inner surface of the upper section, the inner surface of the lower section, or both;
providing a second base drape material having an upper edge and a lower edge both extending in a longitudinal direction and a first side edge and a second side edge both extending in a transverse direction to define a perimeter, wherein the second base drape material includes a second longitudinal fold line, wherein a second zone of pockets is located on a surface of the second base drape material;
folding the first base drape material at the first longitudinal fold line to cover any instruments, medical supplies, or a combination thereof so that the instruments, medical supplies, or a combination thereof contained in the first zone of pockets are available for use first during the multi-step sequential procedure after unfolding the first base drape material at the first longitudinal fold line; and
folding the second base drape material at the second longitudinal fold line to cover any instruments, medical supplies, or a combination thereof so that the instruments, medical supplies, or a combination thereof contained in the second zone of pockets are available for use after unfolding the second base drape material at the second longitudinal fold line, wherein a portion of the first base drape material adjacent the first longitudinal fold line is temporarily joined to a portion of the second based drape material adjacent the upper edge of the second base drape material.

14. The method according to claim 13, wherein the inner surface of the upper section, the inner surface of the lower section, or both include an attachment means to adhere the inner surface of the upper section to the inner surface of the lower section.

15. The method according to claim 13, wherein the second longitudinal fold line divides the second base drape material into an upper section and a lower section each having an inner surface and an outer surface, wherein the second zone of pockets is present on the inner surface of the upper section, the inner surface of the lower section, or both.

16. The method according to claim 13, wherein the first base drape material and the second drape material are separable from each other via a tearable feature extending in the longitudinal direction adjacent the first longitudinal fold line and adjacent the upper edge of the second base drape material.

17. The method according to claim 13, wherein each of the first zone of pockets and the second zone of pockets are formed from a clear material, further wherein a plurality of vertical seals are present in the first zone of pockets and the second zone of pockets to define individual pockets in each of the first zone of pockets and the second zone of pockets.

18. The method according to claim 13, wherein the first zone of pockets and the second zone of pockets each include a free end and a sealed end.

19. The method according to claim 13, wherein a boundary exists between the perimeter of the first base drape material and the first zone of pockets, the second base drape material and the second zone of pockets, or both, wherein the boundary spans a distance ranging from about 40 millimeters to about 150 millimeters.

20. The method according to claim 13, wherein the first base drape material, the second base drape material, or both is formed from a sterilization material.

21. The method according to claim 13, wherein the multi-step sequential procedure is selected from procedures for abdominal aortic aneurysm repair; limb amputation; appendix surgery; AV shunt for dialysis; bile duct, liver, or pancreatic surgery; breast surgery; cardiac surgery; coronary bypass with chest and donor incisions; coronary bypass graft; carotid endarterectomy; gallbladder surgery; colon surgery; craniotomy; cesarean section; spinal fusion; open reduction of fracture; gastric surgery; herniorrhaphy; hip prosthesis; heart transplant; abdominal hysterectomy; knee prosthesis; kidney transplant; laminectomy; liver transplant; neck surgery; kidney surgery; ovarian surgery; pacemaker surgery; prostate surgery; peripheral vascular bypass surgery; rectal surgery; small bowel surgery; spleen surgery; thoracic surgery; thyroid and/or parathyroid surgery; vaginal hysterectomy; ventricular shunt; and exploratory laparotomy.

\* \* \* \* \*